United States Patent
Feng et al.

(10) Patent No.: US 11,654,198 B2
(45) Date of Patent: *May 23, 2023

(54) APPLICATION OF COMBINATION OF POLYETHYLENE GLYCOL AND LOCAL ANESTHETIC IN NON-NARCOTIC ANALGESIA

(71) Applicant: JENKEM TECHNOLOGY CO., LTD. (TIANJIN), Tianjin (CN)

(72) Inventors: Zewang Feng, Beijing (CN); Jinliang Wang, Beijing (CN); Yanli Xiong, Beijing (CN); Juan Shi, Beijing (CN); Xuan Zhao, Beijing (CN)

(73) Assignee: JENKEM TECHNOLOGY CO., LTD. (TIANJIN), Tianjin (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/473,437

(22) PCT Filed: Dec. 22, 2017

(86) PCT No.: PCT/CN2017/117956
§ 371 (c)(1),
(2) Date: Jun. 25, 2019

(87) PCT Pub. No.: WO2018/121427
PCT Pub. Date: Jul. 5, 2018

(65) Prior Publication Data
US 2020/0147228 A1    May 14, 2020

(30) Foreign Application Priority Data

Dec. 29, 2016  (CN) .......................... 201611247317.0
Sep. 30, 2017  (CN) .......................... 201710937900.2

(51) Int. Cl.
| | | |
|---|---|---|
| *A61K 47/60* | (2017.01) | |
| *A61K 31/167* | (2006.01) | |
| *A61K 31/4458* | (2006.01) | |
| *A61P 23/02* | (2006.01) | |
| *A61K 47/54* | (2017.01) | |
| *A61K 9/00* | (2006.01) | |

(52) U.S. Cl.
CPC ............. *A61K 47/60* (2017.08); *A61K 9/0019* (2013.01); *A61K 31/167* (2013.01); *A61K 31/4458* (2013.01); *A61K 47/545* (2017.08); *A61P 23/02* (2018.01)

(58) Field of Classification Search
CPC .... A61K 47/60; A61K 9/0019; A61K 31/167; A61K 31/4458; A61K 47/545; A61K 9/107; A61K 9/127; A61K 9/19; A61K 9/2018; A61K 9/2054; A61K 9/2059; A61K 9/2866; A61K 47/02; A61K 31/445; A61K 45/06; A61K 45/00; A61P 23/02
See application file for complete search history.

(56) References Cited

FOREIGN PATENT DOCUMENTS

CN          110960685 A  *  4/2020
WO    WO-2011139595 A2  * 11/2011   ........... A61K 9/0024

* cited by examiner

*Primary Examiner* — Savitha M Rao
*Assistant Examiner* — Andrew P Lee
(74) *Attorney, Agent, or Firm* — Platinum Intellectual Property

(57) ABSTRACT

The invention discloses use of a conjugate of polyethylene glycol and a local anesthetic in non-anesthetic analgesia. A local anesthetic is prepared into a prodrug or a sustained release preparation, wherein a high molecular polymer such as polyethylene glycol in the prodrug is covalently bonded with a local anesthetic, and auxiliary materials with a sustained release effect in the sustained release preparation are non-covalently bonded to the local anesthetic. After administration, there is no anesthesia and analgesic effect before the release of the free local anesthetic. After the free local anesthetic is released, an analgesic effect is achieved. And the prodrug or the sustained-release preparation of the local anesthetic of the present invention releases the drug slowly, and renders the drug concentration kept stable and long-lasting in the effective concentration range of non-narcotic analgesia, and the long-acting non-anesthetic analgesic effect can be achieved while significantly reducing the clinical adverse reactions of local anesthetics and reducing the number of administrations. The effectiveness of the drug is greatly enhanced and the clinical application range of local anesthetics is expanded.

2 Claims, No Drawings

APPLICATION OF COMBINATION OF POLYETHYLENE GLYCOL AND LOCAL ANESTHETIC IN NON-NARCOTIC ANALGESIA

RELATED APPLICATIONS

This application is a United States National Stage Application filed under 35 U.S.C 371 of PCT Patent Application Serial No. PCT/CN2017/117956, filed Dec. 22, 2017, which claims Chinese Patent Application Serial No. CN 201611247317.0, filed Dec. 29, 2016; and Chinese Patent Application Serial No. CN 201710937900.2, filed Sep. 30, 2017, the disclosure of all of which are hereby incorporated by reference in their entirety.

TECHNICAL FIELD

The present invention relates to the technical field of medicine, in particular to use of a conjugate of polyethylene glycol and a local anesthetic in non-anesthetic analgesia, especially long-acting non-anesthetic analgesia.

BACKGROUND

Chronic pain, especially postoperative pain, is a common clinical symptom. The diseases involved include various clinical departments. While making patients feel painful, the diseases itself also produce a series of pathophysiological changes, such as affecting the autonomic nervous system of the body, increased heart rate, shortness of breath, and rising blood pressure; affecting emotions, leading to dysphoria, depression, and then affecting the recovery of the digestive system function and physical strength; affecting endocrine and hormone levels, and disturbing the body internal environment directly and indirectly. Therefore, reasonable analgesia can play the following roles: (1) alleviating the pain and discomfort of the patient, relieving anxiety, and improving sleep; enabling the patient to get through the postoperative stage in a more comfortable state; (2) eliminating unwillingness to breathe deeply and cough caused by pains, improving breathing, promoting sputum excretion, and reducing lung infections; (3) relieving pain, prompting patients to get out of bed early and functional exercise early, and reducing the risk of deep vein thrombosis caused by bed-ridden for a long time; (4) blocking sympathetic overexcitation, eliminating tension, dilating blood vessels, improving microcirculation, thereby promoting wound healing and accelerating postoperative rehabilitation; (5) inhibiting sympathetic activity, promoting gastrointestinal motility, and helping to restore the gastrointestinal function after surgery; and (6) reducing the hospitalization time and saving costs by reducing complications and accelerating recovery.

Many primary symptoms of the chronic pain are not easy to eliminate, and symptomatic pain is often treated with symptomatic treatment. Partial block therapy is generally used, especially with local anesthetics. They can temporarily and completely reversibly block nerve conduction within a limited range of the human body, that is, to lose a sense of a certain part of the human body when the consciousness has not disappeared, thereby playing an analgesic role. For example, bupivacaine can be used alone or in combination with fentanyl or morphine for postoperative patient-controlled epidural analgesia. Compared with general anesthesia, local anesthesia can greatly reduce the impact on the patient's physiological function, so local anesthetics are widely used for nerve block anesthesia, epidural anesthesia and so on. However, with the wide application of local anesthetics in clinical practice, its toxic side effects have become increasingly prominent, such as local adverse reactions such as local tissue reactions, nervous tissue reactions, cytotoxic reactions, systemic adverse reactions such as hypersensitivity reactions, allergies (such as airway edema, bronchospasm, dyspnea, urticaria, etc.), central nervous system toxic reactions (such as perioral numbness, headache, dizziness, tinnitus, blurred vision, muscle twitching, confusion, convulsions, etc.), cardiotoxic reactions (such as tachycardia, hypertension, arrhythmia, and inhibition of the myocardial contractile function) and so on described in "Li Shuai, Li Wanli. Adverse reactions and prevention of local anesthetics. Journal of Naval Medicine, 2011 (4): 383-383", specifically the prominent manifestation of the severe toxicity of local anesthetic is convulsion. At this time, due to the uncoordinated and strong contraction of the airway and chest and abdominal muscles, it is bound to affect the respiratory and cardiovascular systems, which may be life-threatening. The occurrence of these adverse reactions will additionally increase the patient's pain and risk, significantly reducing patient compliance.

Through experiments and studies, the inventors of the present invention have found that reducing the dosage of local anesthetics to a suitable range can achieve non-anesthetic analgesic effects, and can reduce some adverse reactions of local anesthetics, such as reduced motor nerve block effects on experimental animals, but the non-anesthetic analgesic effect is maintained for a short period of time. For example, the non-anesthetic analgesic effect of a single dose of bupivacaine can only be maintained for at most 1 hour. For analgesia, especially chronic pain, frequent administration is required to achieve long-acting analgesic effects, the use is very inconvenient, the compliance of patients who need analgesia is not conducive, and the high-low dose window of local anesthetics that can be used for non-anesthetic analgesia is very small and difficult to control. Thus administration of local anesthetics separately is not suitable for non-anesthetic analgesia. However, the inventors of the present invention have made a local anesthetic into a prodrug or a sustained release preparation, particularly a conjugate of polyethylene glycol and a local anesthetic, and surprisingly found that non-anesthetic analgesia, in particular, long-acting non-anesthetic analgesic effects, can be achieved by slow release of the drug, such as PEG-bupivacaine conjugates, can be maintained for 48 hours, 72 hours or longer. While significantly reducing or even eliminating motor blockade, the number of doses is significantly reduced, patient compliance is greatly improved, and the clinical application range of local anesthetics is expanded.

SUMMARY

The invention provides a use of a local anesthetic release system for preparation of a medicament for non-anesthetic analgesia.

Preferably, the local anesthetic release system comprises a prodrug of a local anesthetic, and a sustained release preparation of a local anesthetic;

Preferably, the concentration of free local anesthetics released in the local tissue and/or systemic part is maintained between a minimum anesthetic dose and a minimum analgesic dose of the local anesthetic after administration of the local anesthetic delivery system.

Preferably, the local anesthetic is an amide local anesthetic, more preferably one or more selected from the group consisting of lidocaine, prilocaine, bupivacaine, ropivacaine, mepivacaine and etidocaine.

In one embodiment of the present invention, the local anesthetic is bupivacaine or ropivacaine, and it has been experimentally found that bupivacaine can be locally administered to the vicinity of the sciatic nerve in rats at a concentration of 0.00625% to 0.0625% to achieve non-anaesthetic analgesic effects, and ropivacaine can be administered to the vicinity of the sciatic nerve in rats at a concentration of 0.01% to 0.2% to achieve non-anaesthetic analgesic effects.

Preferably, the prodrug of the local anesthetic is obtained by bonding a local anesthetic to a high molecular polymer such as polyethylene glycol.

The sustained release preparation of the local anesthetic in the present invention refers to a preparation for delaying the release rate of the local anesthetic from the dosage form and reducing the absorption rate of the medicine into the body, thereby achieving a better therapeutic effect; according to different preparation processes thereof, the sustained release preparation of the local anesthetic comprises: a skeleton-dispersed sustained-release preparation (the drug is dispersed in a skeleton material, and the sustained release is achieved by dissolution or dissolution of the skeleton material or diffusion of the drug in the skeleton material), and a film controlled sustained-release preparation (a drug is incorporated in a film coating, microcapsules, etc., and the sustained release is achieved by controlling the thickness of the film, micropore diameter, curvature of the micropore, etc.), a sustained-release emulsion (such as a drug is prepared into a W/O emulsion, and the sustained release is achieved by using the barrier effect of an oil phase on drug molecular diffusion), a sustained release liposome (a drug is encapsulated in a lipid-like bilayer to form micro-vesicles, and the sustained release of the drug is achieved through changes of the bilayer structure), etc.

Preferably, the local anesthetic release system is a prodrug of a local anesthetic.

In a preferred embodiment of the present invention, the prodrug of the local anesthetic is a conjugate of polyethylene glycol and a local anesthetic, and the local anesthetic can use polyethylene glycol as a carrier, so that the local anesthetic remains in the lesions for a longer period of time, and then the local anesthetic is degraded from the conjugate chain to achieve sustained release and controlled release, and the prodrug of the local anesthetic has a structure of a formula (I):

PEG-A-R$_0$—B         (I)

Wherein, PEG is a polyethylene glycol residue having a molecular weight of 1-100 KDa;

R$_0$ is a C$_{1-6}$ alkyl group, preferably, R$_0$ is a methyl group (—CH$_2$—), an ethyl group (—CH$_2$CH$_2$—) or a propyl group (—CH$_2$CH$_2$CH$_2$—), more preferably, R$_0$ is a methyl group (—CH$_2$—);

B is a local anesthetic;

A quaternary ammonium salt having a structure of

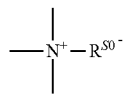

is formed at the junction of B and R$_0$, R$^{s0}$ is selected from a group consisting of: F$^-$, Cl$^-$, Br$^-$, I$^-$, mesylate, ethylsulfonate, benzenesulfonate, citrate, lactate, succinate, fumarate, glutamate, citrate, salicylate and maleate; preferably, R$^{s0}$ is selected from a group consisting of: F$^-$, Cl$^-$, Br$^-$, I$^-$, mesylate, ethylsulfonate and benzenesulfonate; most preferably, R$^{s0}$ is selected from a group consisting of: F$^-$, Cl$^-$, Br$^-$ and I$^-$;

A is a linking group selected from a structure shown by the following formula A$_1$ or A$_2$:

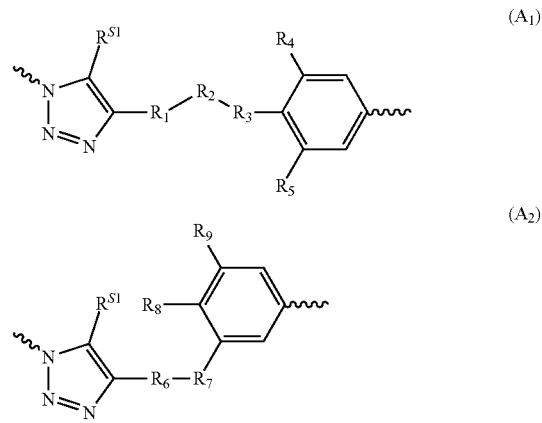

Wherein, R$_1$ and R$_6$ are independently selected from a C$_{1-6}$ alkyl group, preferably a methyl group (—CH$_2$—), an ethyl group (—CH$_2$CH$_2$—) or a propyl group (—CH$_2$CH$_2$CH$_2$—), or R$_1$ and R$_6$ are independently selected from —(CH$_2$)$_i$NHCO(CH$_2$)$_j$—, —(CH$_2$)$_i$CONH(CH$_2$)$_j$—, i and j are independently an integer selected from 0 to 6, preferably 1, 2 or 3;

R$_2$ is selected from —C═O, —C═S, —O— or —S—, preferably —C═O, —O— or —S—;

R$_3$ and R$_7$ are independently selected from —O— or —S—;

R$_4$ and R$_5$ are independently selected from H, C$_{1-6}$ alkyl or halogen (F$^-$, Cl$^-$, Br$^-$ or I$^-$), preferably H, a methyl group (—CH$_3$) or an ethyl group (—CH$_2$CH$_3$), most preferably H or a methyl group (—CH$_3$);

R$_8$ and R$_9$ are independently selected from H, C$_{1-6}$ alkyl or —O(C═O)(CH$_2$)$_i$CH$_3$, i is an integer selected from 0 to 6, preferably 1, 2 or 3, preferably H, a methyl group (—CH$_3$), an ethyl group (—CH$_2$CH$_3$), a propyl group (—CH$_2$CH$_2$CH$_2$—), acetoxy, propionyloxy or butyryloxy; most preferably, R$_8$ is acetoxy, propionyloxy or butyryloxy, and R$_9$ is H or methyl (—CH$_3$);

R$^{s1}$ is selected from H or C$_{1-6}$ alkyl, preferably H, a methyl group (—CH$_3$), an ethyl group (—CH$_2$CH$_3$) or a propyl group (—CH$_2$CH$_2$CH$_3$).

The PEG of the present invention is a linear or branched PEG (2-10-arm branched PEG), including linear PEG, double-ended PEG, 2-arm branched PEG, 4-arm branched PEG, 6-arm branched PEG or 8-arm branched PEG or the like. The molecular weight of PEG is between 1 KDa and 100 KDa, for example, 1 to 10 KDa (specifically 1, 2, 3, 4, 5, 6, 7, 8, 9 or 10 KDa), 10 to 50 KDa (specifically 10, 15, 20, 25, 30, 35, 40, 45 or 50 KDa) or 50 to 100 KDa (specifically 50, 55, 60, 65, 70, 75, 80, 85, 90, 95 or 100 KDa), etc. Preferably, the PEG has a molecular weight of 10 to 50 KDa, most preferably 10 to 40 KDa, such as between 10 KDa and 20 KDa, between 20 KDa and 25 KDa, between 25 KDa and 30 KDa, between 30 KDa and 35 KDa, or between 35 KDa and 40 KDa.

In some embodiments, the PEG can be a linear, double-ended, Y-type or multi-branched polyethylene glycol residue.

Preferably, the PEG is a linear polyethylene glycol residue having a structure of a formula (II-1):

(II-1)

Wherein, m is a positive integer of 200-1000, such as 200, 250, 300, 450 or 600.

Preferably, the PEG is a Y-type polyethylene glycol having the structure of a formula (II-2):

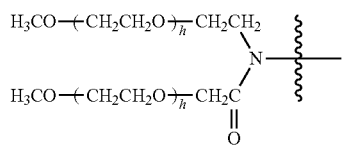
(II-2)

Wherein, h is an integer from 10 to 1000, and preferably, h is an integer from 100 to 500.

When the PEG is a multi-branched polyethylene glycol, the conjugate has a structure of a formula (II-3) to a formula (II-5):

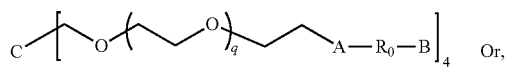
(II-3)

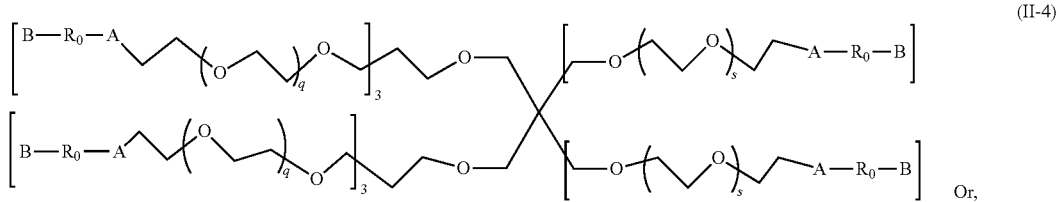
(II-4)

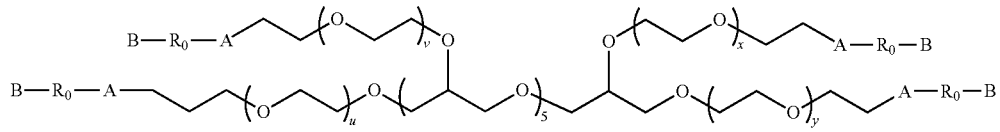
(II-5)

Wherein, q is selected from an integer from 5 to 500, preferably, q is an integer from 50 to 250;

s, t, u, v, x and y are independently selected from an integer from 2 to 250, preferably, s, t, u, v, x and y are independently selected from an integer from 25 to 125.

The use of Y-type or multi-branched polyethylene glycol can increase the drug loading capacity to ensure proper drug concentration and enhance sustained release. When a Y-type or multi-branched polyethylene glycol residue is employed, one or more arms of the multi-branched polyethylene glycol may be optionally attached to one or more linking groups, correspondingly capable of loading more drugs.

In some embodiments, the linking group A of the present invention is selected from a group consisting of structures shown by the following formulas $A_3$-$A_6$:

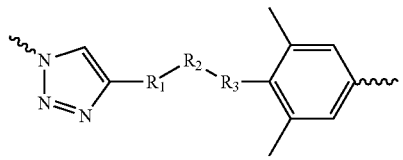
($A_3$)

($A_4$)

($A_5$)

($A_6$)

Wherein, $R_1$ is methyl (—$CH_2$—), ethyl (—$CH_2CH_2$—), propyl (—$CH_2CH_2CH_2$—) or —$(CH_2)_i$NHCO$(CH_2)_j$—, —$(CH_2)_i$CONH$(CH_2)_j$—, i and j are independently selected from 1, 2 or 3;

$R_2$ is —C=O, —O— or —S—;

$R_3$ is —O— or —S—;

$R_8$ is acetoxy, propionyloxy or butyryloxy;

$R_9$ is H or methyl;

p is 1, 2 or 3.

In some embodiments, the local anesthetic of the present invention is an amide local anesthetic having a structure of a formula (III):

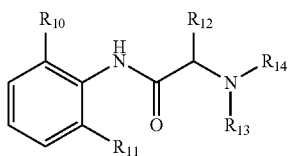

(III)

wherein, $R_{10}$ and $R_{11}$ are independently selected from H or $C_{1-6}$ alkyl, preferably H, a methyl group (—CH$_3$), an ethyl group (—CH$_2$CH$_3$) or a propyl group (—CH$_2$CH$_2$CH$_3$);

$R_{12}$, $R_{13}$ and $R_{14}$ are independently selected from H or $C_{1-6}$ alkyl, preferably H, a methyl group (—CH$_3$), an ethyl group (—CH$_2$CH$_3$), a propyl group (—CH$_2$CH$_2$CH$_3$) or a butyl group (—CH$_2$CH$_2$CH$_2$CH$_3$); or $R_{13}$ is selected from H, or $C_{1-6}$ alkyl, a 5-8-membered ring is formed between N and $R_{12}$ and $R_{14}$, preferably a 6-membered ring.

Preferably, the local anesthetic may be lidocaine, prilocaine, bupivacaine, ropivacaine, mepivacaine or etidocaine.

In some embodiments, the conjugate has a structure of the following formula (IV):

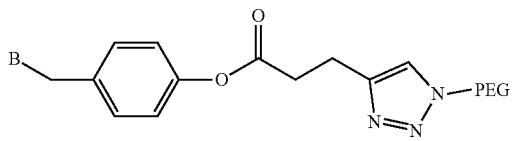

(IV)

Wherein, a quaternary ammonium salt having a structure of

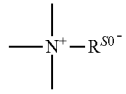

is formed at the junction of B and —CH$_2$—, and $R^{s0}$ is selected from a group consisting of: F$^-$, Cl$^-$, Br$^-$ or I$^-$.

Specifically, when B is bupivacaine, the conjugate structure can be:

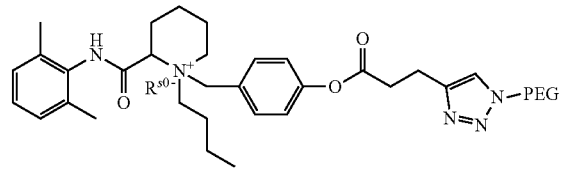

(IV)

Wherein, $R^{s0}$ is selected from a group consisting of: F$^-$, Cl$^-$, Br$^-$ or I$^-$.

Specifically, when B is lidocaine, the conjugate structure can be:

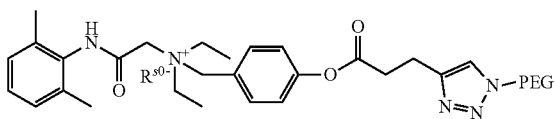

Wherein, $R^{s0}$ is selected from a group consisting of: F$^-$, Cl$^-$, Br$^-$ or I$^-$.

In a specific embodiment of the invention, the conjugate has a structure of the following formula (V):

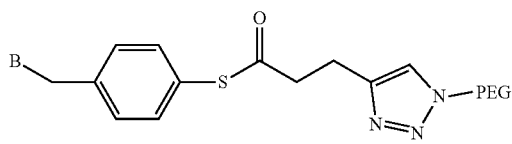

(V)

Wherein, a quaternary ammonium salt having a structure of

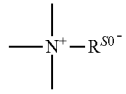

is formed at the junction of B and —CH$_2$—, and $R^{s0}$ is selected from a group consisting of: F$^-$, Cl$^-$, Br$^-$ or I$^-$.

Specifically, when B is bupivacaine, the conjugate structure can be:

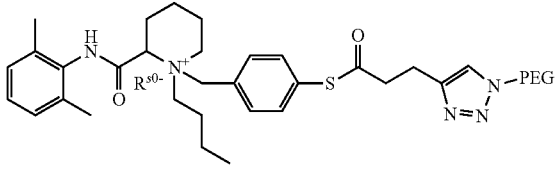

Wherein, $R^{s0}$ is selected from a group consisting of: F$^-$, Cl$^-$, Br$^-$ or I$^-$.

In a specific embodiment of the invention, the conjugate has a structure of the following formula (VI):

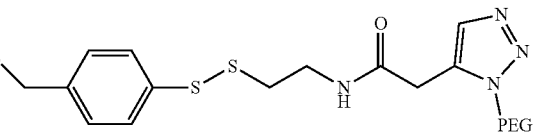

(VI)

Wherein, a quaternary ammonium salt having a structure of

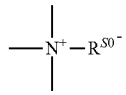

is formed at the junction of B and —CH$_2$—, and R$^{s0}$ is selected from a group consisting of: F$^-$, Cl$^-$, Br$^-$ or I$^-$.

Specifically, when B is bupivacaine, the conjugate structure can be:

Wherein, R$^{s0}$ is selected from a group consisting of: F$^-$, Cl$^-$, Br$^-$ or I$^-$.

In a specific embodiment of the invention, the conjugate has a structure of the following formula (VII):

(VII)

Wherein, a quaternary ammonium salt having a structure of $$-\text{N}^+-\text{R}^{s0-}$$

is formed at the junction of B and —CH$_2$—, and R$^{s0}$ is selected from a group consisting of: F$^-$, Cl$^-$, Br$^-$ or I$^-$.

Specifically, when B is bupivacaine, the conjugate structure can be:

Wherein, R$^{s0}$ is selected from a group consisting of: F$^-$, C$^-$, Br$^-$ or I$^-$.

In a specific embodiment of the invention, the conjugate has a structure of the following formula (VIII):

(VIII)

Wherein, a quaternary ammonium salt having a structure of $$-\text{N}^+-\text{R}^{s0-}$$

is formed at the junction of B and —CH$_2$—, and R$^{s0}$ is selected from the group consisting of: F$^-$, Cl$^-$, Br$^-$ or I$^-$.

Specifically, when B is bupivacaine, the conjugate structure can be:

Wherein, R$^{s0}$ is selected from a group consisting of: F$^-$, Cl$^-$, Br$^-$ or I$^-$.

In a specific embodiment of the invention, the conjugate has a structure of the following formula (IX):

(IX)

Wherein, a quaternary ammonium salt having a structure of $$-\text{N}^+-\text{R}^{s0-}$$

is formed at the junction of B and —CH$_2$—, and R$^{s0}$ is selected from a group consisting of: F$^-$, Cl$^-$, Br$^-$ or I$^-$.

Specifically, when B is bupivacaine, the conjugate structure can be:

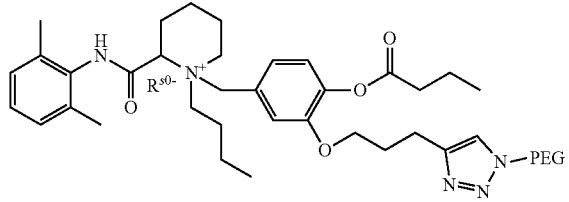

Wherein, $R^{s0}$ is selected from a group consisting of F⁻, Cl⁻, Br⁻ or I⁻.

In a specific embodiment of the invention, the conjugate has a structure of the following formula (X):

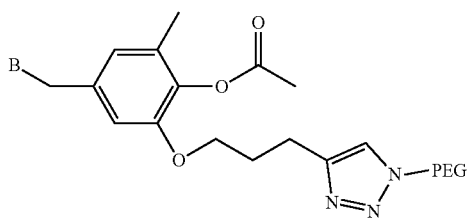

(X)

Wherein, a quaternary ammonium salt having a structure of

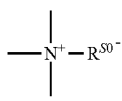

is formed at the junction of B and —CH₂—, and $R^{s0}$ is selected from a group consisting of: F⁻, Cl⁻, Br⁻ or I⁻.

Specifically, when B is bupivacaine, the conjugate structure can be:

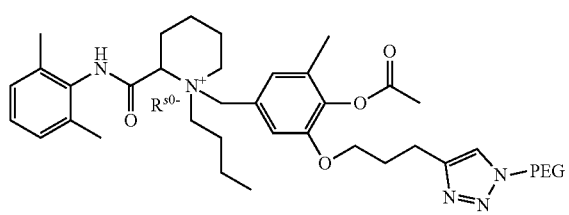

Wherein, $R^{s0}$ is selected from a group consisting of: F⁻, Cl⁻, Br⁻ or I⁻.

In a specific embodiment of the invention, the conjugate has a structure of the following formula (XI):

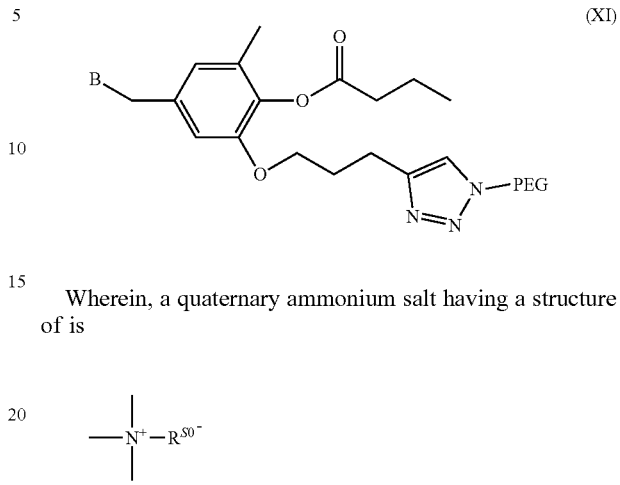

(XI)

Wherein, a quaternary ammonium salt having a structure of is formed at the junction of B and —CH₂—, and $R^{s0}$ is selected from a group consisting of: F⁻, Cl⁻, Br⁻ or I⁻.

Specifically, when B is bupivacaine, the conjugate structure can be:

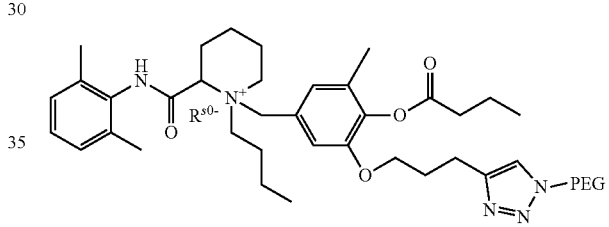

Wherein, $R^{s0}$ is selected from a group consisting of: F⁻, Cl⁻, Br⁻ or I⁻.

In a specific embodiment of the invention, the conjugate has a structure of the following formula (XII):

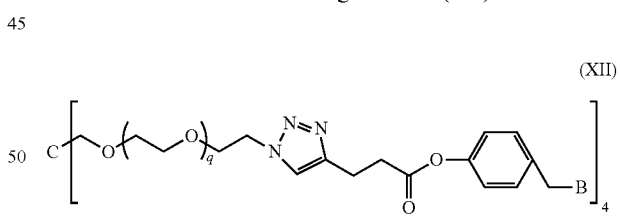

(XII)

Wherein, a quaternary ammonium salt having a structure of is formed at the junction of B and —CH₂—, and $R^{s0}$ is selected from a group consisting of: F⁻, Cl⁻, Br⁻ or I⁻, and q is the same as the above definition in the formula II-3 of the present invention.

In a specific embodiment of the invention, the conjugate has a structure of the following formula (XIII):

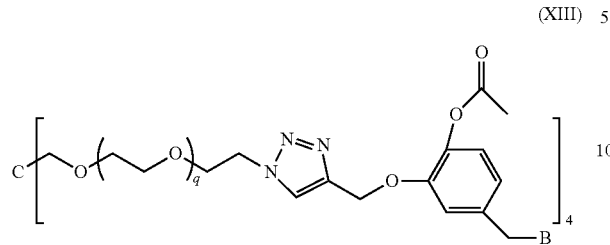

Wherein, a quaternary ammonium salt having a structure of

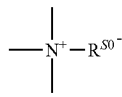

is formed at the junction of B and —CH$_2$—, and R$^{s0}$ is selected from a group consisting of: F$^-$, Cl$^-$, Br$^-$ or I$^-$, and q is the same as the above definition in the formula II-3 of the present invention.

In a specific embodiment of the invention, the conjugate has a structure of the following formula (XIV):

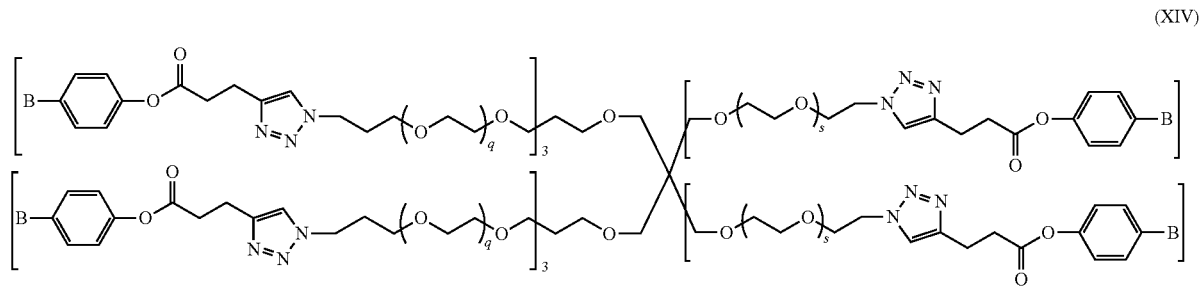

Wherein, a quaternary ammonium salt having a structure of

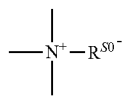

is formed at the junction of B and —CH$_2$—, R$^{s0}$ is selected from a group consisting of: F$^-$, Cl$^-$, Br$^-$ or I$^-$, and s and t are the same as the above definition in the formula II-4 of the present invention.

In a specific embodiment of the invention, the conjugate has a structure of the following formula (XV):

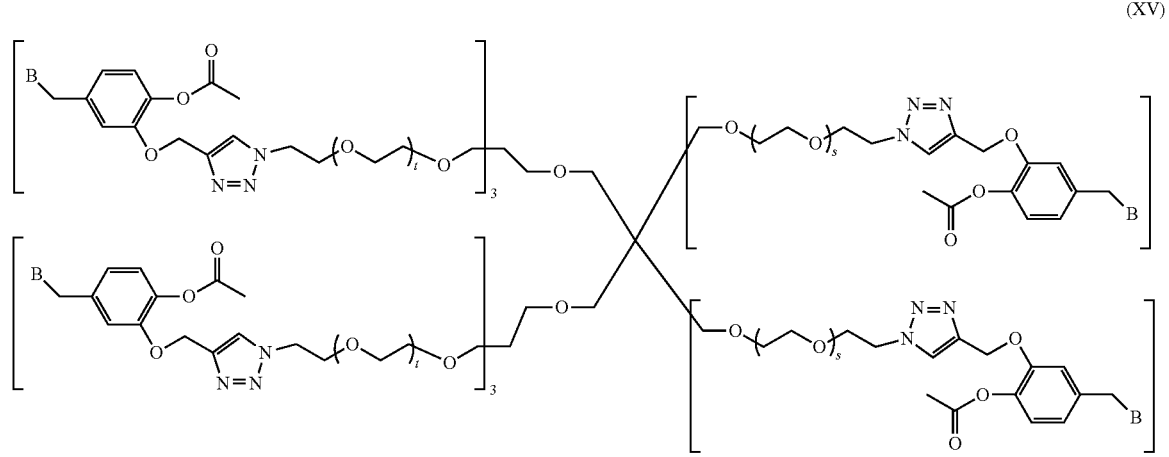

Wherein, a quaternary ammonium salt having a structure of

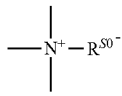

is formed at the junction of B and —CH$_2$—, R$^{s0}$ is selected from a group consisting of: F$^-$, Cl$^-$, Br$^-$ or I$^-$, and s and t are the same as the above definition in the formula II-4 of the present invention.

In a specific embodiment of the invention, the conjugate has a structure of the following formula (XVI):

(XVI)

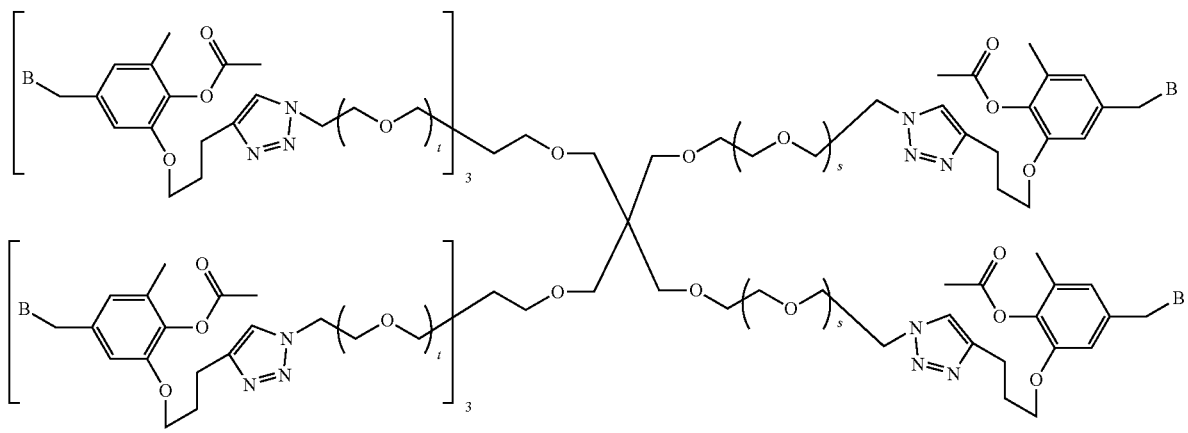

Wherein, a quaternary ammonium salt having a structure of

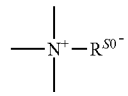

is formed at the junction of B and —CH$_2$—, R$^{s0}$ is selected from a group consisting of: F$^-$, Cl$^-$, Br$^-$ or I$^-$, and s and t are the same as the above definition in the formula II-4 of the present invention.

In a specific embodiment of the invention, the conjugate has a structure of the following formula (XVII):

(XVII)

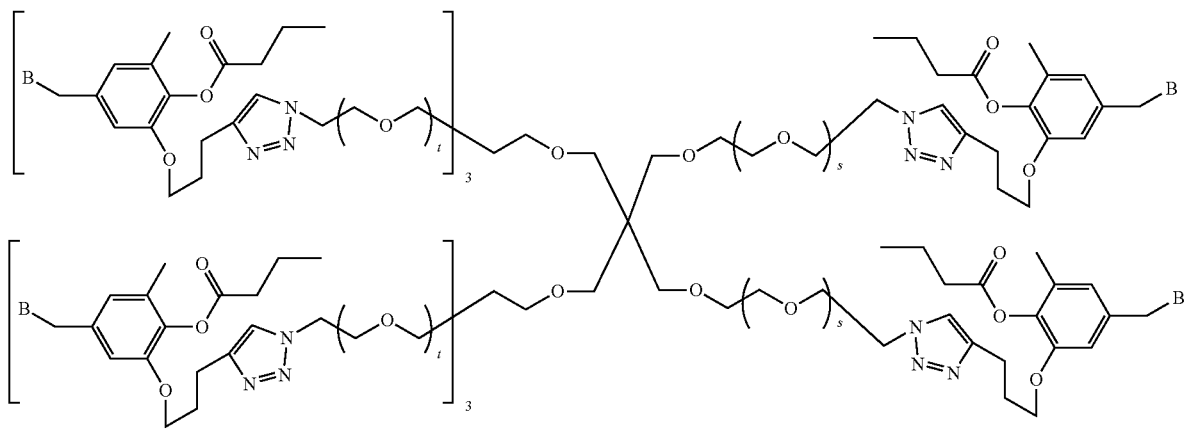

Wherein, a quaternary ammonium salt having a structure of

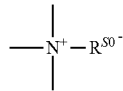

is formed at the junction of B and —CH$_2$—, R$^{s0}$ is selected from a group consisting of: F$^-$, Cl$^-$, Br$^-$ or I$^-$, and s and t are the same as the above definition in the formula II-4 of the present invention.

In a specific embodiment of the invention, the conjugate has a structure of the following formula (XVIII):

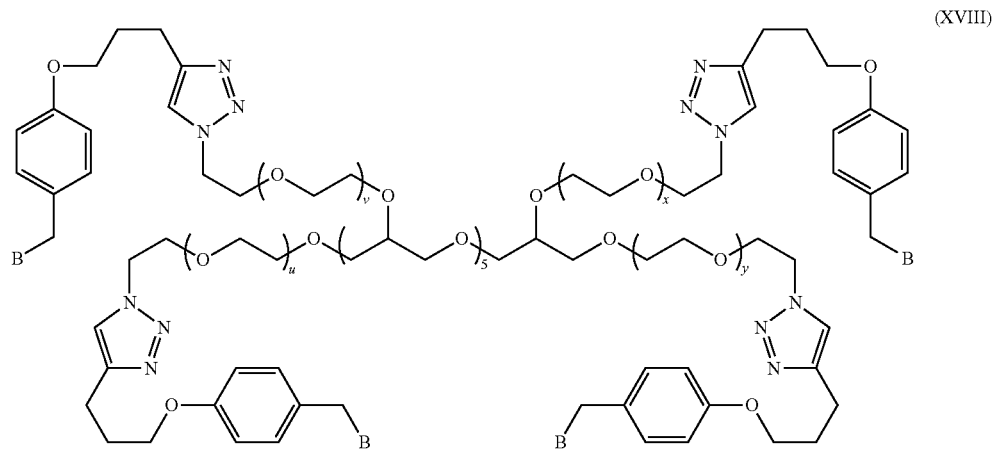

Wherein, a quaternary ammonium salt having a structure of

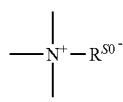

is formed at the junction of B and —CH$_2$—, R$^{s0}$ is selected from a group consisting of: F$^-$, Cl$^-$, Br$^-$ or I$^-$, and u, v, x and y are the same as the above definition in the formula II-5 of the present invention.

In a specific embodiment of the invention, the conjugate has a structure of the following formula (XIX):

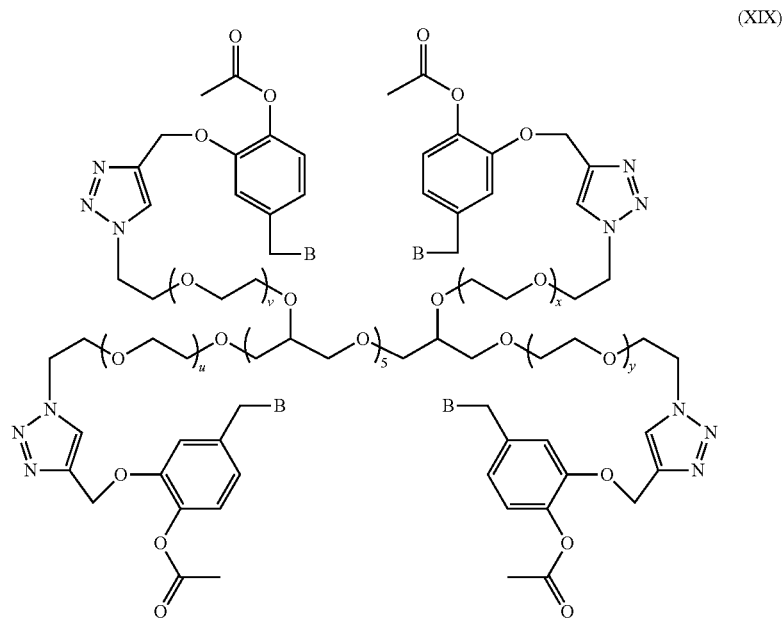

Wherein, a quaternary ammonium salt having a structure of

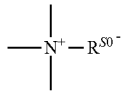

is formed at the junction of B and —CH$_2$—, R$^{s0}$ is selected from a group consisting of: F$^-$, Cl$^-$, Br$^-$ or I$^-$, and u, v, x and y are the same as the above definition in the formula II-5 of the present invention. The invention also provides use of a pharmaceutical composition comprising the above conjugate and a pharmaceutically acceptable carrier or an excipient thereof for the preparation of a medicament for non-anesthetic analgesia.

In some embodiments, the pharmaceutical composition will comprise from about 1 to about 99% by weight of the above conjugate, and from 99 to 1% by weight of a suitable carrier or a pharmaceutically acceptable excipient, depending on a mode of administration desired. Preferably, the composition comprises from about 5 to 75% by weight of the above conjugate, with the balance being a suitable carrier or a pharmaceutically acceptable excipient. More preferably, the composition comprises from about 10 to 50% by weight of the above conjugate, with the balance being a suitable carrier or a pharmaceutically acceptable excipient.

In some embodiments, the pharmaceutical composition of the present invention may further comprise minor amounts of auxiliary substances such as wetting or emulsifying agents, pH buffering agents or antioxidants, etc., for example: citric acid, sorbitan monolaurate, triethanolamine oleate or butylated hydroxytoluene and so on.

In some embodiments, the dosage form of the pharmaceutical composition is a tablet, a capsule, a pill, a granule, a powder, a suppository, an injection, a solution, a powder-injection, a suspension, a paste, a patch, a lotion, a drop, a liniment, an aerosol or a spray.

In some embodiments, the above conjugate may be administered in a form of a pure compound or a suitable pharmaceutical composition, and may be administered by using any acceptable mode of administration or agents for similar uses. Thus, the mode of administration employed may be selected by oral, intranasal, parenteral, topical, transdermal or rectal administration in the form of a solid, semi-solid or liquid pharmaceutical form, for example, tablets, suppositories, pills, soft and hard gelatin capsules, powders, solutions, suspensions, injections and the like, preferably unit dose forms suitable for simple administration of precise doses are employed.

The pharmaceutical composition which can be administered in a liquid form, for example, can be dissolved or dispersed in a carrier by dissolving, dispersing the above conjugates (about 0.5 to about 20%) and optionally a pharmaceutically acceptable adjuvant, to form solutions or suspensions. Examples of carriers are water, saline, aqueous dextrose, glycerol or ethanol, etc.

The invention prepares a local anesthetic into a prodrug or a sustained release preparation, wherein a high molecular polymer in the prodrug such as polyethylene glycol is covalently bonded with a local anesthetic, and auxiliary materials with a sustained release effect in the sustained release preparation are non-covalently bonded with the local anesthetic. After the administration of the prodrug or sustained release preparation of the above local anesthetic (especially for topical administration), there is no anesthesia and analgesia effect before the free local anesthetics are released. After the free local anesthetics are released to the surroundings of the nerves of the skin or muscle, the analgesia effect is achieved. And the prodrug (such as a PEG-local anesthetic conjugate) or a sustained-release preparation of the local anesthetic of the present invention releases the drug slowly, renders the drug concentration kept stable and long-lasting in the effective concentration range of non-narcotic analgesia, and the long-acting non-anesthetic analgesic effect can be achieved while significantly reducing the clinical adverse reactions of local anesthetics and reducing the number of administrations. The effectiveness of the drug is enhanced, patient compliance is greatly improved and the clinical application range of local anesthetics is expanded.

DETAILED DESCRIPTION OF THE EMBODIMENTS

The technical solutions of the present invention will be described clearly and completely in conjunction with the examples of the present invention. It is obvious that the described examples are only a part of the examples of the present invention, and not all of the examples. All other examples obtained by those skilled in the art based on the examples of the present invention without creative efforts are within the scope of the present invention.

The polyethylene glycol used in the examples was supplied by Beijing Jenkem Technology Co., Ltd., unless otherwise specified, the molecular weight was 20K. Others are commercially available reagents.

Example 1 Synthesis of Linking Chain (L1)

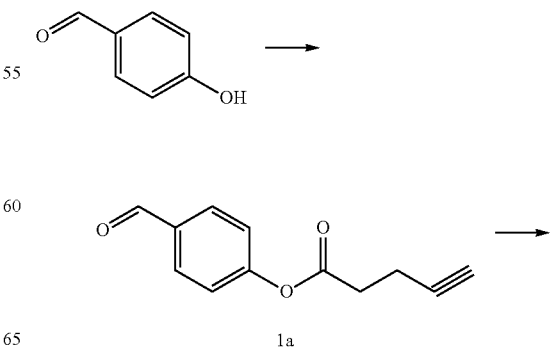

1a

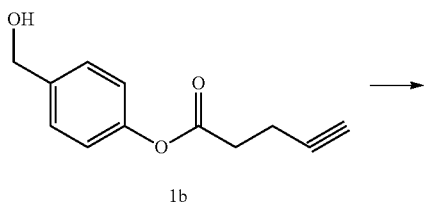

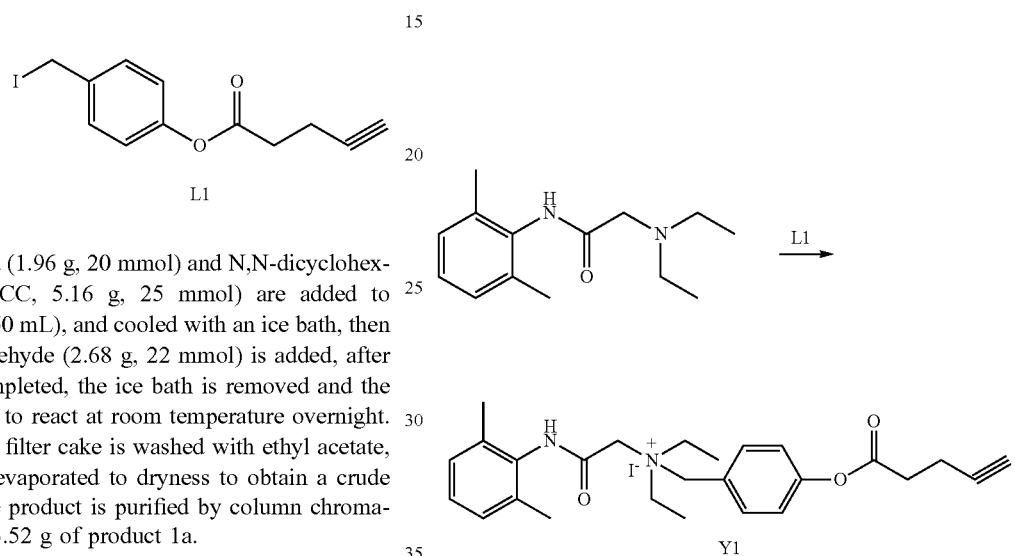

4-Pentynoic acid (1.96 g, 20 mmol) and N,N-dicyclohexylcarbodiimide (DCC, 5.16 g, 25 mmol) are added to dichloromethane (50 mL), and cooled with an ice bath, then p-hydroxy benzaldehyde (2.68 g, 22 mmol) is added, after the addition is completed, the ice bath is removed and the mixture is allowed to react at room temperature overnight. After filtration, the filter cake is washed with ethyl acetate, and the filtrate is evaporated to dryness to obtain a crude product. The crude product is purified by column chromatography to yield 3.52 g of product 1a.

The compound 1a (3.23 g, 16 mmol) is added anhydrous methanol (35 mL), and cooled to 0° C., then sodium borohydride (365 mg, 9.6 mmol) is added, and a reaction is carried out for 10 min at the same temperature, and then the reaction is quenched with 1 M HCl. The methanol is rotary-evaporated to dryness. The ethyl acetate and saturated brine are added. The aqueous phase is extracted with ethyl acetate, and the organic phases are mixed, washed with saturated brine, dried, filtered and concentrated to obtain a crude product. The crude product is purified by column chromatography to yield 1.80 g of product 1b.

Iodine (3.35 g, 13.2 mmol), triphenylphosphine (3.46 g, 13.2 mmol) and imidazole (0.90 g, 13.2 mmol) are added in dichloromethane (30 mL), and stirred at 0° C. for 20 min, a solution of the product 1b (1.80 g, 8.8 mmol) in dichloromethane (7.5 mL) is added and a reaction is carried out at 0° C. for 30 min. The liquid mixture is washed with 2N hydrochloric acid, saturated sodium bisulfite and brine respectively, dried and evaporated to dryness to obtain a crude product. The crude product is purified by column chromatography to yield 2.41 g of product L1. $^1$H NMR: (CDCl$_3$): 2.03 (s, 1H), 2.61 (t, 2H), 2.77 (t, 2H), 4.44 (s, 2H), 7.01 (d, 2H), 7.39 (d, 2H).

Example 2 Synthesis of Lidocaine Quaternary Ammonium Salt (Y1)

Lidocaine (0.50 g, 2.13 mmol) and the compound L1 (1.00 g, 3.19 mmol) are added to acetonitrile (20 mL) and reacted at 50° C. overnight. TLC monitoring showed that the lidocaine is completely reacted and the reaction solution is concentrated to obtain a crude product. The crude product is purified by column chromatography to yield 1.19 g of product Y1. $^1$H NMR: (CDCl$_3$): 1.59 (m, 6H), 2.06 (s, 2H), 2.31 (s, 6H), 2.64 (m, 2H), 2.87 (m, 2H), 3.49 (m, 2H), 3.71 (m, 2H), 4.89 (s, 2H), 4.93 (s, 2H), 7.06 (m, 3H), 7.28 (d, 2H), 7.62 (d, 2H), 9.79 (s, 1H).

Example 3 Synthesis of Lidocaine Conjugate 1 (mPEG-Lidocaine, 20K)

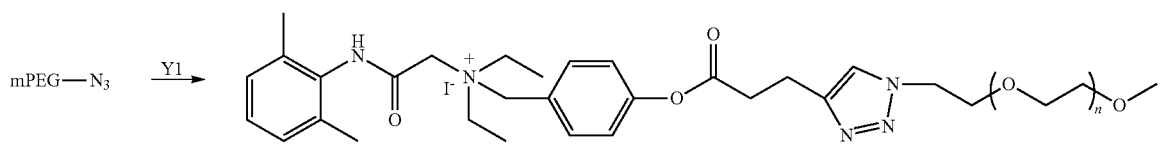

mPEG-N₃ (20K, 2.00 g, 0.10 mmol), the compound Y1 (65.8 mg, 0.12 mmol), and vitamin C (52.8 mg, 0.30 mmol) are added to N,N-dimethylformamide (20 mL), and stirred rapidly to make the above materials dissolved. Then an aqueous solution (4.4 mL, 2.2 mL/g PEG) of copper sulfate pentahydrate (30.0 mg, 0.12 mmol) is added, and the mixture is reacted overnight at room temperature, and precipitation is carried out with isopropyl alcohol to obtain 1.90 g of product. ¹H NMR: (CDCl₃): 1.42 (m, 6H), 2.19 (s, 6H), 3.02 (m, 4H), 3.23 (m, 4H), 3.31 (s, 3H), 3.50 (m, 1800H), 3.80 (m, 2H), 4.20 (m, 2H), 4.50 (s, 2H), 4.82 (s, 2H), 7.12 (m, 3H), 7.30 (d, 2H), 7.64 (d, 2H), 7.91 (s, 1H), 10.28 (s, 1H).

Example 4 Synthesis of Lidocaine Conjugate 2 (4-Arm-PEG-Lidocaine, 10K)

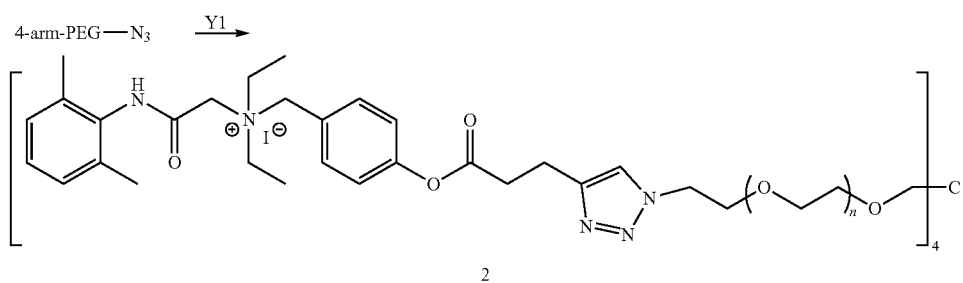

4-arm-PEG-N₃ (10K, 2.00 g, 0.20 mmol), the compound Y1 (548 mg, 1.00 mmol), and vitamin C (440 mg, 2.50 mmol) are added to N,N-dimethylformamide (20 mL), and stirred rapidly to make the above materials dissolved. And then an aqueous solution (4.4 mL, 2.2 mL/g PEG) of copper sulfate pentahydrate (250 mg, 1.00 mmol) is added, and the mixture is reacted overnight at room temperature, and precipitation is carried out with isopropyl alcohol to obtain 1.83 g of product. ¹H NMR: (CDCl₃): 1.43 (m, 24H), 2.22 (s, 24H), 3.07 (m, 16H), 3.25 (m, 16H), 3.34 (s, 12H), 3.50 (m, 900H), 3.83 (m, 8H), 4.22 (m, 8H), 4.53 (s, 8H), 4.85 (s, 8H), 7.13 (m, 12H), 7.30 (d, 8H), 7.65 (d, 8H), 7.92 (s, 4H), 10.26 (s, 4H).

Example 5 Synthesis of Lidocaine Conjugate 3 (8-Arm-PEG-Lidocaine, 20K)

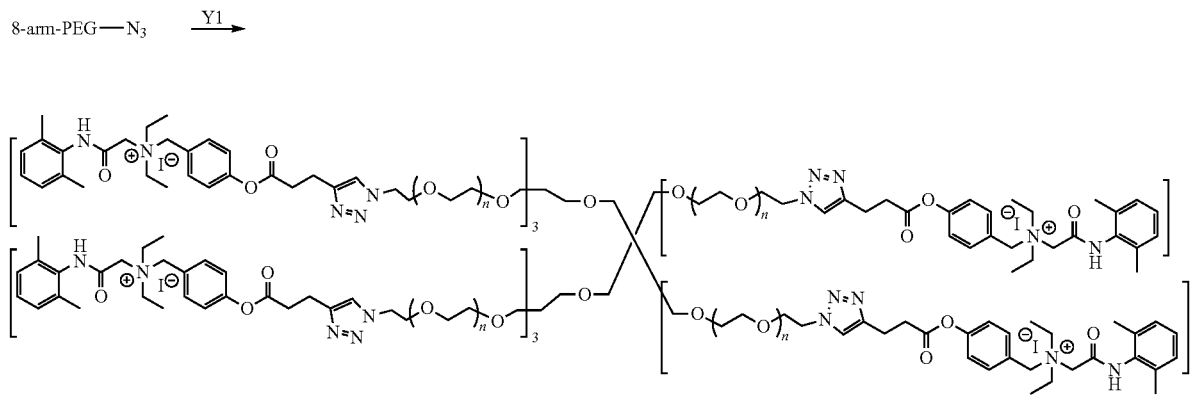

8-arm-PEG-N₃ (20K, 2.00 g, 0.10 mmol), the compound Y1 (548 mg, 1.00 mmol), and vitamin C (440 mg, 2.50 mmol) are added to N,N-dimethylformamide (20 mL), and stirred rapidly to make the above materials dissolved. And then an aqueous solution (4.4 mL, 2.2 mL/g PEG) of copper sulfate pentahydrate (250 mg, 1.00 mmol) is added, and the mixture is reacted at room temperature overnight, and precipitation is carried out with isopropyl alcohol to obtain 1.62 g of product. ¹H NMR: (CDCl₃): 1.44 (m, 48H), 2.22 (s, 48H), 3.09 (m, 32H), 3.23 (m, 32H), 3.37 (s, 24H), 3.51 (m, 1800H), 3.84 (m, 16H), 4.23 (m, 16H), 4.54 (s, 16H), 4.86 (s, 16H), 7.12 (m, 24H), 7.31 (d, 16H), 7.66 (d, 16H), 7.93 (s, 8H), 10.27 (s, 8H).

Example 6 Synthesis of Bupivacaine Quaternary Ammonium Salt (Y2)

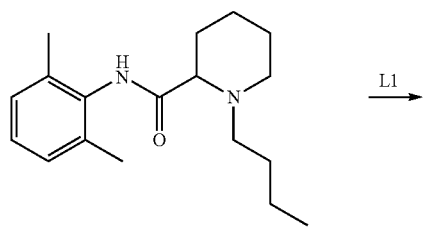

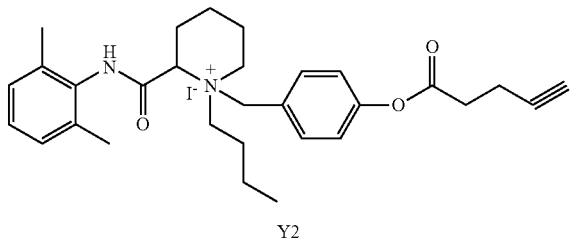

Y2

Bupivacaine (0.50 g, 1.74 mmol) and the compound L1 (1.00 g, 3.19 mmol) are added to acetonitrile (20 mL) and reacted at 50° C. overnight. TLC monitoring showed that the bupivacaine is completely reacted and the reaction solution is concentrated to obtain a crude product. The crude product is purified by column chromatography to yield 0.90 g of product Y2. ¹H NMR: (CDCl₃): 1.09 (m, 3H), 1.46 (m, 3H), 1.85 (m, 4H), 2.19 (m, 1H), 2.30 (s, 6H), 2.61 (m, 2H), 2.76 (m, 2H), 2.93 (s, 1H), 3.30 (m, 2H), 3.39 (m, 2H), 3.71 (m, 2H), 4.91 (s, 2H), 4.96 (s, 2H), 7.18 (m, 3H), 7.26 (d, 2H), 7.42 (d, 2H), 10.15 (s, 1H).

Example 7 Synthesis of Bupivacaine Conjugate 4 (mPEG-Bupivacaine, 20K)

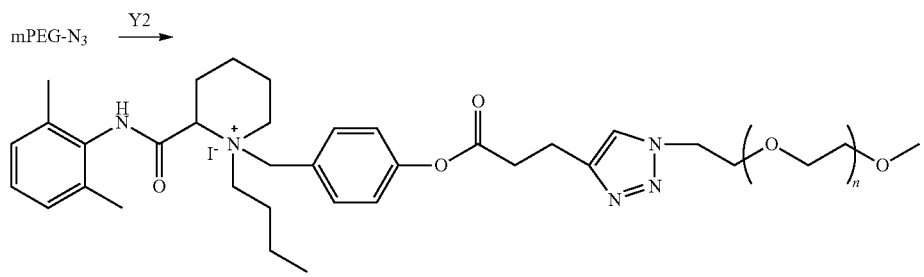

4 mPEG-N₃ (20K, 2.00 g, 0.10 mmol), the compound Y2 (89.7 mg, 0.15 mmol), and vitamin C (52.8 mg, 0.30 mmol) are added to N,N-dimethylformamide (20 mL), and stirred rapidly to make the above materials dissolved. And then an aqueous solution (4.4 mL, 2.2 mL/g PEG) of copper sulfate pentahydrate (30.0 mg, 0.12 mmol) is added, and the mixture is allowed to react overnight at room temperature, and precipitation is carried out with isopropyl alcohol to obtain 1.72 g of product. ¹H NMR: (CDCl₃): 1.09 (m, 3H), 1.25 (m, 1H), 1.37 (m, 3H), 1.75 (m, 4H), 1.97 (m, 1H), 2.16 (s, 6H), 2.23 (m, 1H), 2.57 (m, 2H), 2.85 (m, 2H), 3.27 (m, 4H), 3.32 (s, 3H), 3.56 (m, 1800H), 3.95 (m, 2H), 4.10 (m, 2H), 4.52 (s, 2H), 4.60 (s, 2H), 7.19 (m, 3H), 7.27 (d, 2H), 7.30 (d, 2H), 7.69 (s, 1H), 10.19 (s, 1H).

Example 8 Synthesis of Bupivacaine Conjugate 5
(4-Arm-PEG-Bupivacaine, 10K)

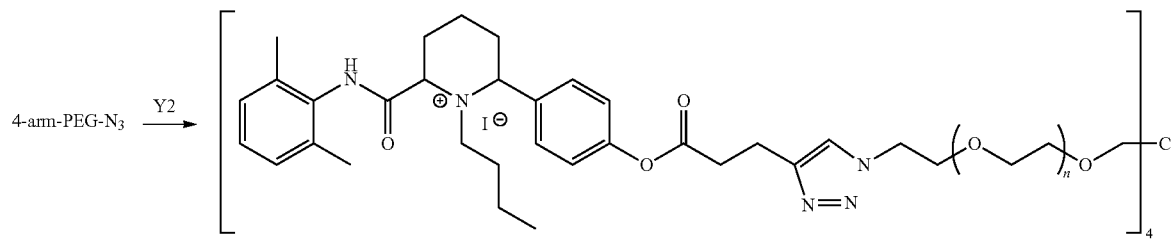

5

4-arm-PEG-N$_3$ (10K, 2.00 g, 0.20 mmol), the compound Y2 (723 mg, 1.20 mmol), and vitamin C (440 mg, 2.50 mmol) are added to N,N-dimethylformamide (20 mL), and stirred rapidly to make the above materials. And then an aqueous solution (4.4 mL, 2.2 mL/g PEG) of copper sulfate pentahydrate (250.0 mg, 1.00 mmol) is added, and the mixture is allowed to react overnight at room temperature, and precipitation is carried out with isopropyl alcohol to obtain 1.82 g of product. $^1$H NMR: (CDCl$_3$): 1.08 (m, 12H), 1.26 (m, 4H), 1.38 (m, 12H), 1.74 (m, 8H), 1.98 (m, 4H), 2.17 (s, 24H), 2.25 (m, 4H), 2.56 (m, 8H), 2.83 (m, 8H), 3.27 (m, 16H), 3.31 (s, 12H), 3.54 (m, 900H), 3.95 (m, 8H), 4.07 (m, 8H), 4.50 (s, 8H), 4.58 (s, 8H), 7.21 (m, 12H), 7.29 (d, 8H), 7.33 (d, 8H), 7.65 (s, 4H), 10.15 (s, 4H).

Example 9 Synthesis of Bupivacaine Conjugate 6
(8-Arm-PEG-Bupivacaine, 20K)

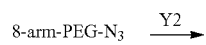

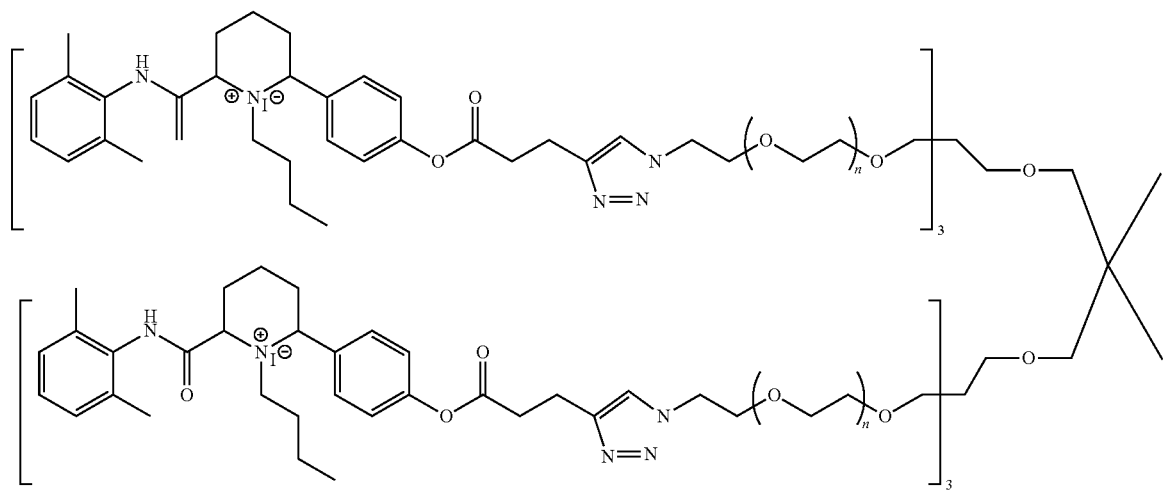

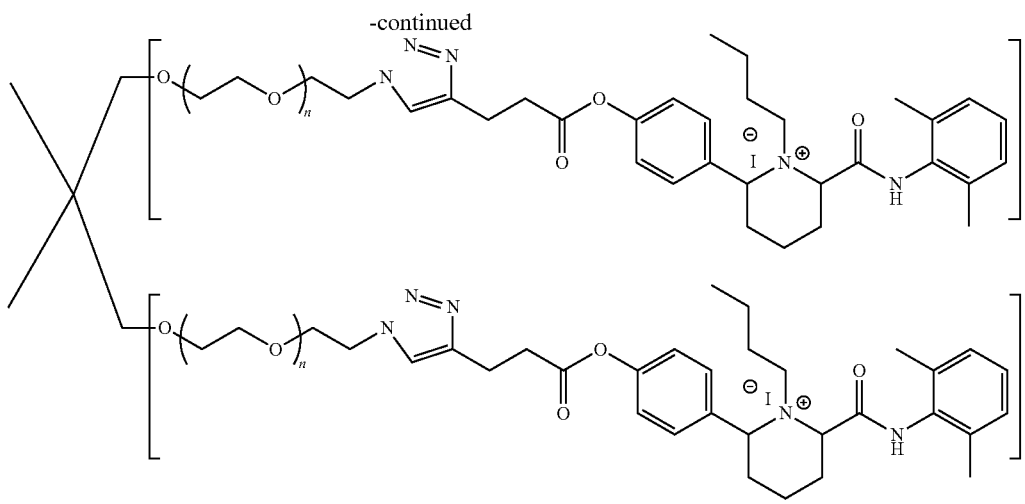

8-arm-PEG-N₃ (20K, 2.00 g, 0.10 mmol), the compound Y2 (723 mg, 1.20 mmol), and vitamin C (440 mg, 2.50 mmol) are added to N,N-dimethylformamide (20 mL), and stirred rapidly to make the above materials dissolved. And then an aqueous solution (4.4 mL, 2.2 mL/g PEG) of copper sulfate pentahydrate (250 mg, 1.00 mmol) is added, and the mixture is allowed to react overnight at room temperature, and precipitation is carried out with isopropyl alcohol to obtain 1.64 g of product. $^1$H NMR: (CDCl₃): 1.09 (m, 24H), 1.26 (m, 8H), 1.39 (m, 24H), 1.73 (m, 16H), 1.97 (m, 8H), 2.17 (s, 48H), 2.24 (m, 8H), 2.57 (m, 16H), 2.81 (m, 16H), 3.27 (m, 32H), 3.32 (s, 24H), 3.51 (m, 1800H), 3.93 (m, 16H), 4.09 (m, 16H), 4.51 (s, 16H), 4.57 (s, 16H), 7.20 (m, 24H), 7.27 (d, 16H), 7.32 (d, 16H), 7.63 (s, 8H), 10.16 (s, 8H).

Example 10 Synthesis of Linked Linking Chain L2

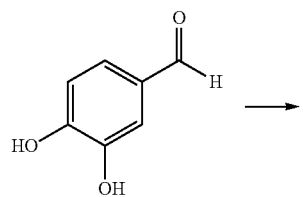

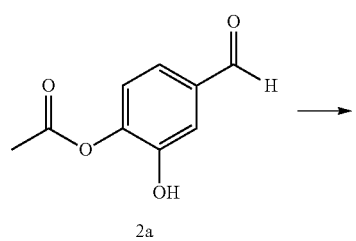
2a

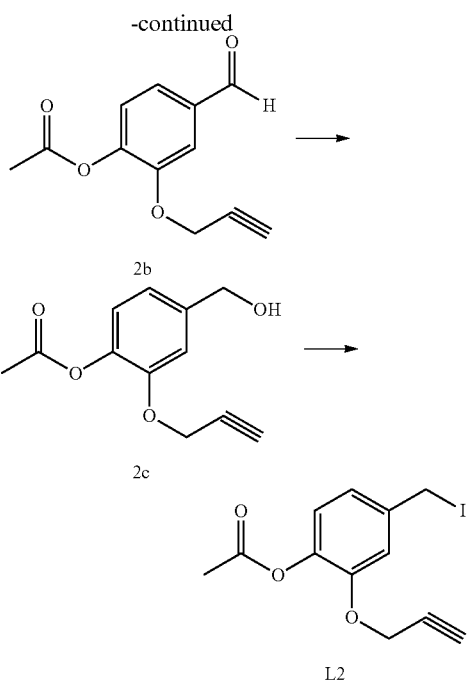

3,4-dihydroxybenzaldehyde (25.0 g, 181 mmol) is added to N,N-dimethylformamide (180 mL), and cooled to 0° C., and sodium hydride (7.2 g, 181 mmol) is added in batches. After addition, the mixture is reacted for 10 minutes, and the temperature is further raised to room temperature. Acetic anhydride (18.7 g, 183 mmol) is added, and after addition, the mixture is reacted for 4 hours. Ice water and 10% hydrochloric acid are added to the reaction liquid, and extraction is carried out with ethyl acetate. The organic phases are mixed, washed with a saturated sodium bicarbonate solution, water and saturated brine respectively and dried. After concentration of the solution, the residue is crystallized by chloroform to obtain 19.8 g of product 2a.

3-Hydroxy-4-acetoxybenzaldehyde (5.40 g, 30 mmol) and sodium carbonate (9.54 g, 90 mmol) are added to N,N-dimethylformamide (50 mL) and heated to 60° C. for reaction for half an hour. Then the reacted material is cooled to room temperature, and a toluene (80%, 4.1 mL) solution of propargyl bromide is added. After the addition is completed, the reaction is continued to be carried out at the same temperature. After the reaction is completed, the mixture is poured into ice water, and the obtained solution is extracted with diethyl ether. The organic phases are mixed, washed with water and dried. After concentration, 5.32 g of product 2b is obtained.

The compound 2b (4.36 g, 20 mmol) is added to absolute methanol (50 mL), and cooled to 0° C., then sodium borohydride (456 mg, 12 mmol) is added, the mixture is reacted for 10 min at the same temperature, and the reaction is quenched with 1 M HCl. The methanol is rotary-evaporated to dryness. The ethyl acetate and saturated brine are added. And the aqueous phase is extracted with ethyl acetate. The organic phases are mixed, washed with saturated brine, dried, filtered and concentrated to obtain a crude product. The crude product is purified by column chromatography to yield 3.30 g of product 2c.

Iodine (3.81 g, 15 mmol), triphenylphosphine (3.93 g, 15 mmol) and imidazole (1.02 g, 15 mmol) are added to dichloromethane (30 mL) and stirred at 0° C. for 20 min. A dichloromethane (10 mL) solution of the product 2c (2.20 g, 10 mmol) is added, and the mixture is reacted at 0° C. for 30 min. The liquid mixture is washed with 2N hydrochloric acid, a saturated sodium bisulfite solution and brine, dried and evaporated to dryness to obtain a crude product. The crude product is purified by column chromatography to yield 2.40 g of product L2. $^1$H NMR: (CDCl$_3$): 2.35 (s, 3H), 3.37 (s, 1H), 4.51 (s, 2H), 4.72 (s, 2H), 6.77 (d, 1H), 7.02 (s, 1H), 7.09 (d, 1H).

Example 11 Synthesis of Lidocaine Quaternary Ammonium Salt Y3

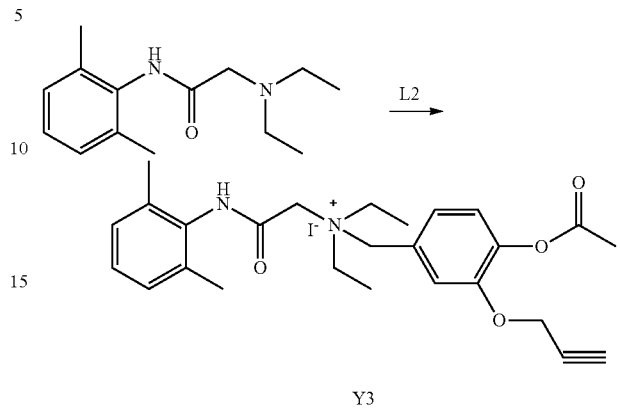

Lidocaine (0.50 g, 2.13 mmol) and the compound L2 (1.08 g, 3.27 mmol) are added to acetonitrile (20 mL) and reacted at 50° C. overnight. TLC monitoring showed that the lidocaine is completely reacted and the reaction solution is concentrated to obtain a crude product. The crude product is purified by column chromatography to yield 0.71 g of product Y3. $^1$H NMR: (CDCl$_3$): 1.05 (m, 6H), 2.13 (s, 2H), 2.30 (s, 3H), 2.42 (m, 4H), 3.31 (s, 2H), 3.35 (s, 1H), 3.63 (m, 2H), 4.71 (s, 2H), 6.92 (d, 1H), 7.08 (d, 1H), 7.12 (s, 1H), 7.19 (m, 3H), 9.82 (s, 1H).

Example 12 Synthesis of Lidocaine Conjugate 7 (4-Arm-PEG-Lidocaine, 10K)

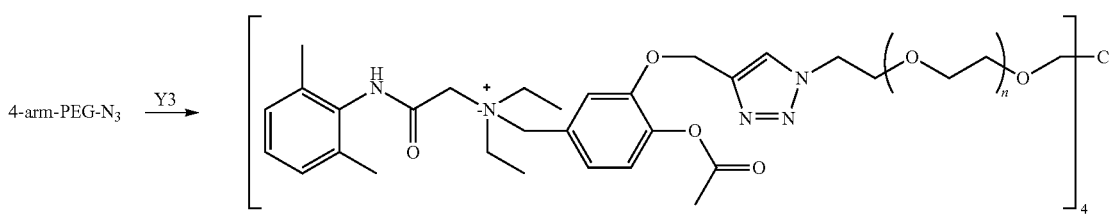

4-arm-PEG-N$_3$ (10K, 2.00 g, 0.20 mmol), the compound Y3 (677 mg, 1.20 mmol), and vitamin C (440 mg, 2.50 mmol) are added to N,N-dimethylformamide (20 mL), and stirred rapidly to make the above materials dissolved. And then an aqueous solution (4.4 mL, 2.2 mL/g PEG) of copper sulfate pentahydrate (250 mg, 1.00 mmol) is added, and the mixture is allowed to react overnight at room temperature, and precipitation is carried out with isopropyl alcohol to obtain 1.83 g of product. $^1$H NMR: (CDCl$_3$): 1.05 (m, 24H), 2.13 (s, 24H), 2.30 (s, 12H), 2.42 (m, 16H), 3.50 (s, 8H), 3.53 (m, 900H), 3.86 (m, 8H), 3.91 (m, 8H), 4.55 (s, 8H), 4.81 (s, 8H), 5.23 (s, 8H), 6.91 (d, 4H), 7.06 (s, 4H), 7.20 (m, 12H), 7.68 (s, 4H), 10.26 (s, 4H).

Example 13 Synthesis of Lidocaine Conjugate 8 (8-Arm-PEG-Lidocaine, 20K)

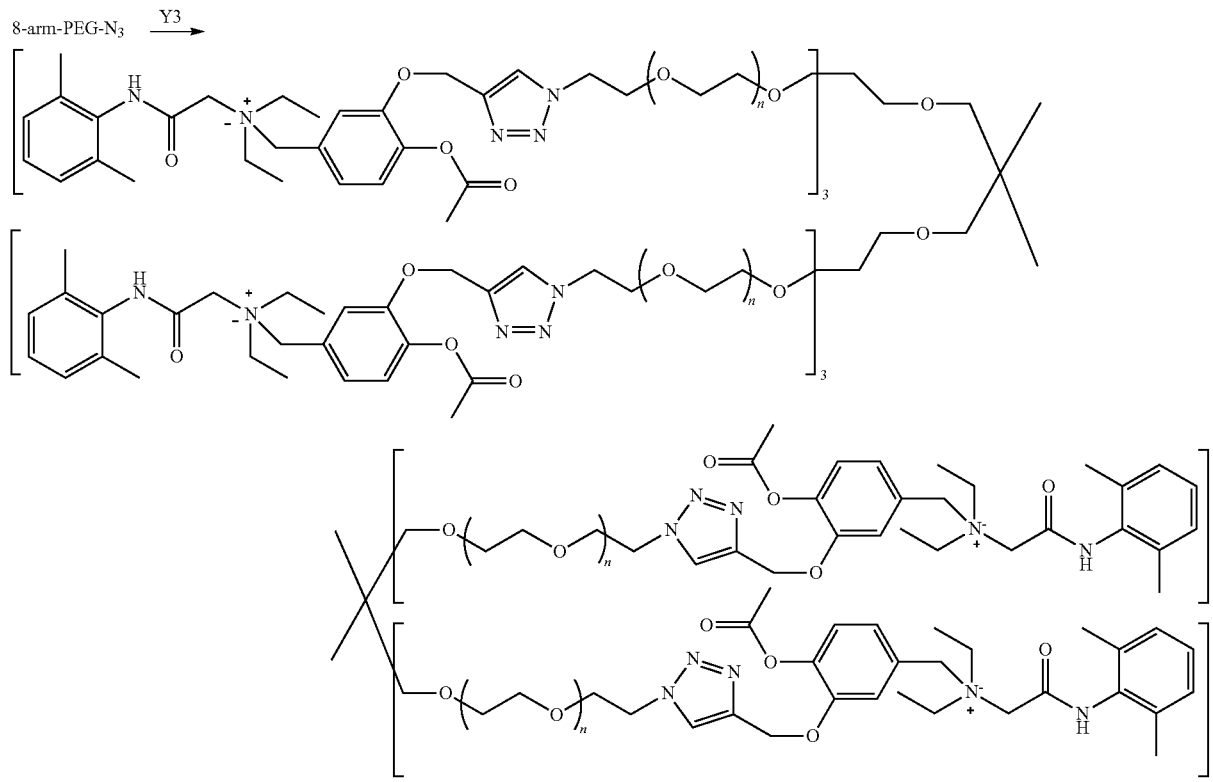

8

8-arm-PEG-N₃ (20K, 2.00 g, 0.10 mmol), the compound Y3 (677 mg, 1.20 mmol), and vitamin C (440 mg, 2.50 mmol) are added to N,N-dimethylformamide (20 mL), and stirred rapidly to make the above materials dissolved. And then an aqueous solution (4.4 mL, 2.2 mL/g PEG) of copper sulfate pentahydrate (250 mg, 1.00 mmol) is added, and the mixture is allowed to react overnight at room temperature, and precipitation is carried out with isopropyl alcohol to obtain 1.70 g of product. ¹H NMR: (CDCl₃): 1.07 (m, 48H), 2.14 (s, 48H), 2.31 (s, 24H), 2.41 (m, 32H), 3.52 (s, 16H), 3.54 (m, 1800H), 3.79 (m, 16H), 3.92 (m, 16H), 4.53 (s, 16H), 4.82 (s, 16H), 5.22 (s, 16H), 6.90 (d, 8H), 7.09 (s, 8H), 7.28 (m, 24H), 7.69 (s, 8H), 10.27 (s, 8H).

Example 14 Synthesis of Bupivacaine Quaternary Ammonium Salt (Y4)

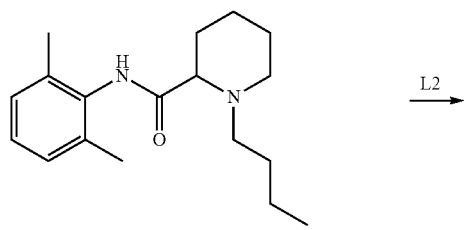

-continued

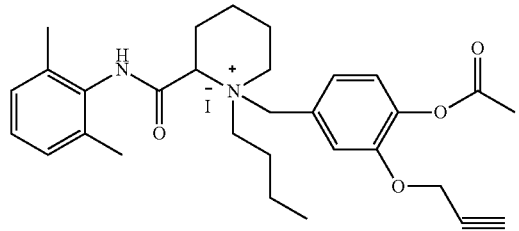

Y4

Bupivacaine (0.50 g, 1.73 mmol) and the compound L2 (1.08 g, 3.27 mmol) are added to acetonitrile (20 mL) and reacted at 50° C. overnight. TLC monitoring showed that the bupivacaine is completely reacted and the reaction solution is concentrated to obtain a crude product. The crude product is purified by column chromatogram to yield 0.75 g of product Y4. ¹H NMR: (CDCl₃): 1.09 (m, 3H), 1.25 (m, 1H), 1.33 (m, 3H), 1.72 (m, 3H), 1.95 (m, 1H), 2.13 (s, 6H), 2.20 (m, 1H), 2.30 (s, 6H), 3.20 (m, 1H), 3.25 (m, 2H), 3.29 (m, 1H), 3.34 (s, 1H), 4.57 (s, 2H), 4.69 (s, 2H), 4.75 (s, 2H), 6.90 (d, 1H), 7.05 (d, 1H), 7.09 (d, 1H), 7.18 (m, 3H), 10.07 (s, 1H).

Example 15 Synthesis of Bupivacaine Conjugate 9 (4-Arm-PEG-Bupivacaine, 10K)

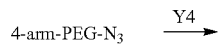

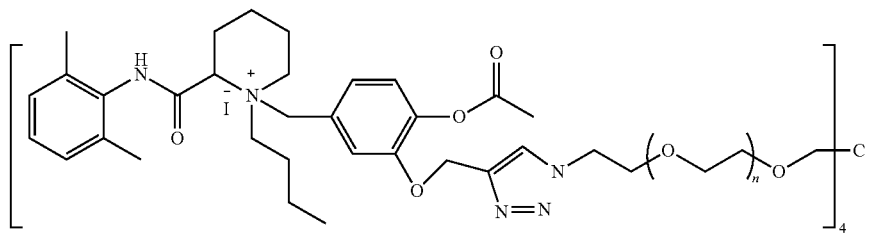

9

4-arm-PEG-N$_3$ (10K, 2.00 g, 0.20 mmol), the compound Y4 (748 mg, 1.20 mmol), and vitamin C (440 mg, 2.50 mmol) are added to N,N-dimethylformamide (20 mL), and stirred rapidly to make the above materials dissolved. And then an aqueous solution (4.4 mL, 2.2 mL/g PEG) of copper sulfate pentahydrate (250 mg, 1.00 mmol) is added, and the mixture is allowed to react overnight at room temperature, and precipitation is carried out with isopropyl alcohol to obtain 1.82 g of product. $^1$H NMR: (CDCl$_3$): 1.09 (m, 12H), 1.25 (m, 4H), 1.33 (m, 12H), 1.72 (m, 12H), 1.95 (m, 4H), 2.13 (s, 24H), 2.20 (m, 4H), 2.30 (s, 24H), 3.20 (m, 4H), 3.25 (m, 8H), 3.28 (m, 4H), 3.50 (s, 8H), 3.54 (m, 900H), 3.86 (m, 8H), 3.91 (m, 8H), 4.52 (s, 8H), 4.59 (s, 8H), 5.23 (s, 8H), 6.82 (d, 4H), 7.03 (d, 4H), 7.09 (s, 4H), 7.18 (m, 12H), 7.65 (s, 4H), 10.13 (s, 4H).

Example 16 Synthesis of Bupivacaine Conjugate 10 (8-Arm-PEG-Bupivacaine, 20K)

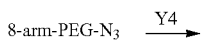

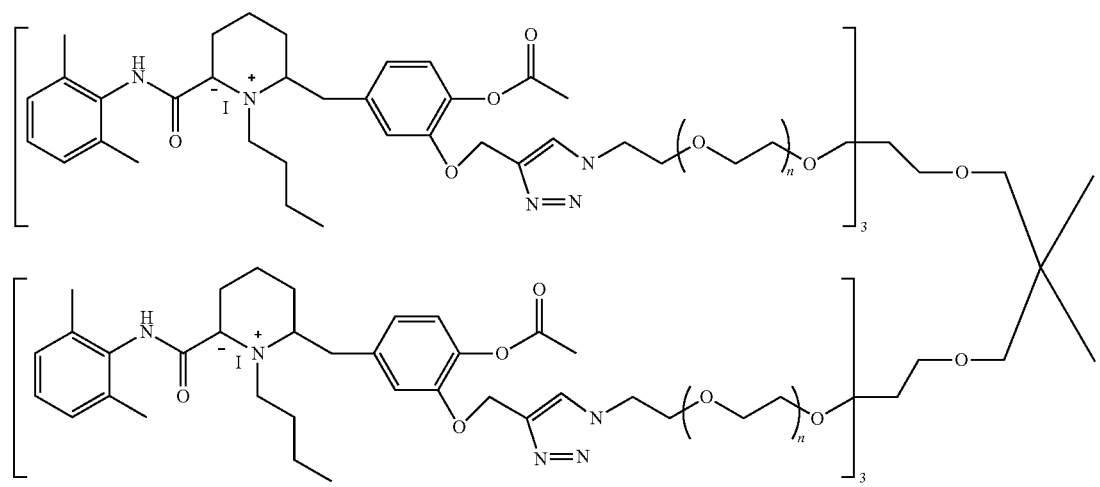

-continued

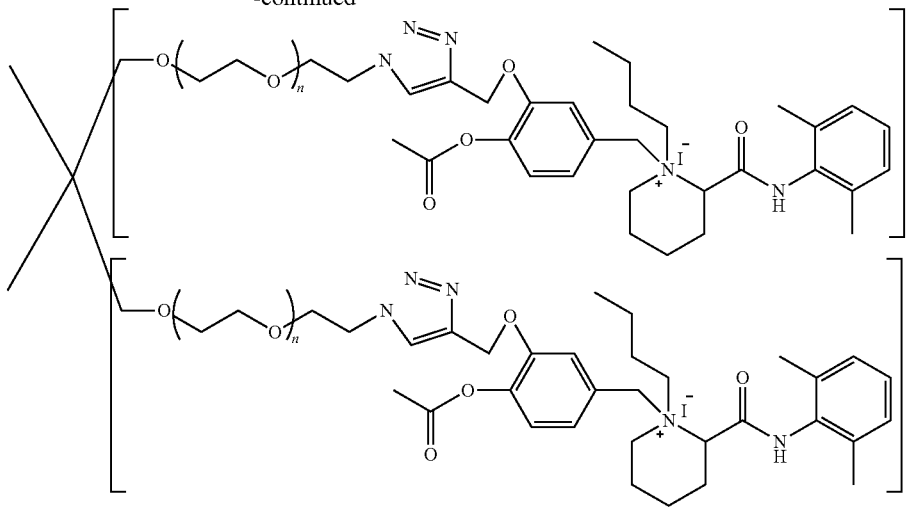

10

8-arm-PEG-N₃ (20K, 2.00 g, 0.10 mmol), the compound Y4 (748 mg, 1.21 mmol), and vitamin C (440 mg, 2.50 mmol) are added to N,N-dimethylformamide (20 mL), and stirred rapidly to make the above materials dissolved. And then an aqueous solution (4.4 mL, 2.2 mL/g PEG) of copper sulfate pentahydrate (250 mg, 1.00 mmol) is added, and the mixture is allowed to react overnight at room temperature, and precipitation is carried out with isopropyl alcohol to obtain 1.61 g of product. ¹H NMR: (CDCl₃): 1.08 (m, 24H), 1.24 (m, 8H), 1.34 (m, 24H), 1.73 (m, 24H), 1.93 (m, 8H), 2.14 (s, 48H), 2.21 (m, 8H), 2.31 (s, 48H), 3.21 (m, 8H), 3.25 (m, 16H), 3.28 (m, 8H), 3.50 (s, 16H), 3.53 (m, 1800H), 3.85 (m, 16H), 3.92 (m, 16H), 4.53 (s, 16H), 4.59 (s, 16H), 5.22 (s, 16H), 6.81 (d, 8H), 7.05 (d, 8H), 7.09 (s, 8H), 7.19 (m, 24H), 7.67 (s, 8H), 10.12 (s, 8H).

Example 17 Synthesis of Linking Chain (L3)

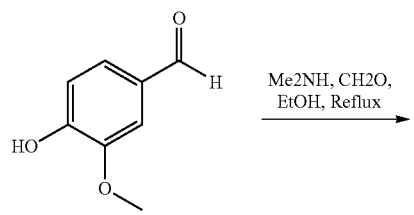 Me2NH, CH2O, EtOH, Reflux →

3a

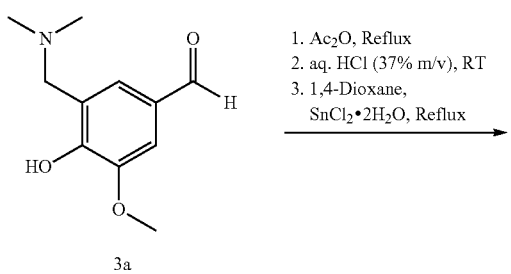 1. Ac₂O, Reflux
2. aq. HCl (37% m/v), RT
3. 1,4-Dioxane, SnCl₂·2H₂O, Reflux →

-continued

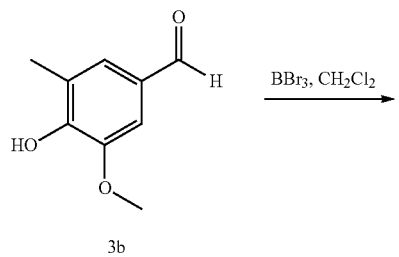 BBr₃, CH₂Cl₂ →

3b

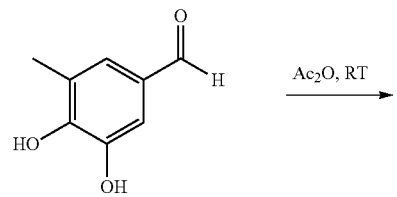 Ac₂O, RT →

3c

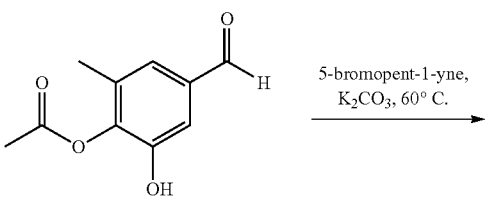 5-bromopent-1-yne, K₂CO₃, 60° C. →

3d

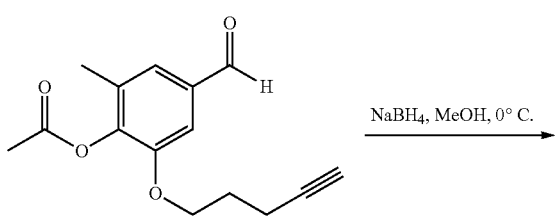 NaBH₄, MeOH, 0° C. →

3e

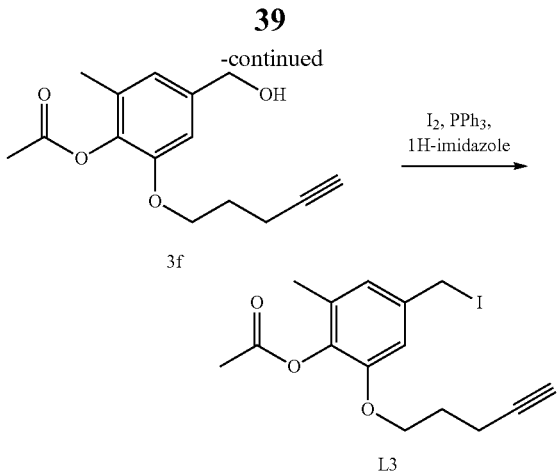

An aqueous formaldehyde solution (37% m/v, 28 mL, 375 mmol), an aqueous dimethylamine solution (40% m/v, 48 mL, 375 mmol) and absolute ethanol (250 mL) are added to a three-necked flask. 4-Hydroxy-3-methoxybenzaldehyde (38.9 g, 250 mmol) is added with stirring, and the mixture is heated to reflux and stirred for 45 minutes, then cooled to room temperature and stirred overnight. After filtration, the filter cake is washed with ice cold acetone and dried at room temperature under reduced pressure to yield 39.1 g of product 3a.

3a (21.0 g, 100 mmol) is dissolved in acetic anhydride (100 mL), and the mixture is heated to reflux under a nitrogen atmosphere and stirred for 24 hours. The reaction mixture is concentrated under reduced pressure. The residue is diluted with HCl (37% m/v, 100 mL) and stirred at room temperature for 2 hours. 1,4-Dioxane (100 mL) and stannous chloride dihydrate (69.8 g, 300 mmol) are added, and the mixture is heated to reflux and stirred for 45 minutes. After cooling to room temperature, hydrochloric acid (37% m/v, 20 mL) is added and then extraction is carried out with dichloromethane (5×100 mL). The mixed extract is washed successively with 6N hydrochloric acid, distilled water and an aqueous sodium chloride solution of 10%, and dried over anhydrous sodium sulfate, and a solvent is evaporated under reduced pressure. The residue is separated and purified with a silica gel column to yield 11.2 g of product 3b. 3b (8.35 g, 50 mmol) is dissolved in dichloromethane (200 mL), stirred and cooled to 0° C., then a solution of boron tribromide in dichloromethane (1M, 150 mmol, 150 mL) is slowly added dropwise under the protection of nitrogen. After adding dropwise, stirring is continued to be performed at 0° C. for 1 hour, and then the temperature is raised to room temperature and stirring is carried out overnight. After cooled to 0° C., the stirred material is diluted by slowly adding distilled water (350 mL), and the organic solvent is evaporated under reduced pressure, and after cooling to room temperature, filtering is carried out. The filter cake is washed with distilled water, transferred to a dry box and dried under reduced pressure to obtain a crude product. The crude product is separated and purified by using silica gel column to yield 5.73 g of product 3c.

3c (27.5 g, 181 mmol) is added to N,N-dimethylformamide (180 mL), cooled to 0° C., sodium hydride (7.2 g, 181 mmol) is added in batches, and a reaction is carried out for 10 minutes. After heating to room temperature, acetic anhydride (18.7 g, 183 mmol) is added, and a reaction is carried out for 4 hours. Ice water and 10% hydrochloric acid are added to the reaction liquid, and the reaction liquid is extracted with ethyl acetate. The organic phases are mixed, washed with a saturated sodium bicarbonate solution, water and saturated brine respectively and dried. After the solution is concentrated, the residue is crystallized with chloroform to yield 19.3 g of product 3d.

3d (17.5 g, 90 mmol) and sodium carbonate (28.6 g, 270 mmol) are added to N,N-dimethylformamide (150 mL), heated to 60° C. for reaction for half an hour, and then cooled to room temperature, and 5-bromopent-1-yne (19.8 g, 135 mmol) is added, and the reaction is continued to be carried out at the same temperature. After the completion of the reaction, the mixture is poured into ice water, and the resulting solution is extracted with diethyl ether. The organic phases are mixed, washed with water and dried. After concentration, 15.9 g of product 3e is obtained.

3e (15.6 g, 60 mmol) is added to absolute methanol (150 mL), and cooled to 0° C., and then sodium borohydride (1.82 g, 48 mmol) is added. The reaction is carried out at the same temperature for 10 min, quenched with 1 M HCl. The methanol is rotary-evaporated to dryness. The ethyl acetate and saturated brine are added. And the aqueous phase is extracted with ethyl acetate. The organic phases are mixed, washed with saturated brine and dried. After filtration, the filtrate is concentrated to obtain a crude product. The crude product is purified by column chromatography to yield 10.5 g of product 3f.

Iodine (11.4 g, 45 mmol), triphenylphosphine (11.8 g, 45 mmol) and imidazole (3.06 g, 45 mmol) are added to dichloromethane (90 mL) and stirred at 0° C. for 20 min, a solution of 3f (7.87 g, 30 mmol) in dichloromethane (30 mL) is added, and the mixture is reacted at 0° C. for 30 min. The liquid mixture is washed with 2N hydrochloric acid, a saturated sodium bisulfite solution and brine, dried and evaporated to dryness to obtain a crude product. The crude product is purified by column chromatography to yield 7.42 g of product L3. $^1$H NMR: (DMSO-$d_6$): 1.79-1.90 (m, 2H), 2.06 (s, 3H), 2.24-2.31 (m, 5H), 2.81 (m, 1H), 3.90-4.08 (m, 2H), 4.57 (s, 2H), 6.92 (d, 1H), 7.02 (d, 1H).

Example 18 Synthesis of Bupivacaine Quaternary Ammonium Salt (Y5)

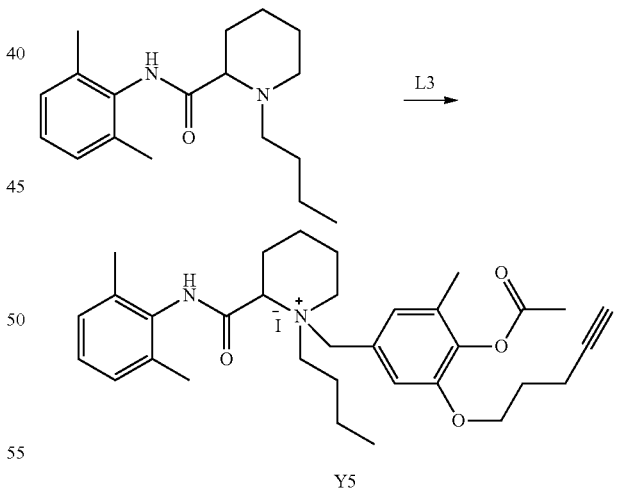

Bupivacaine (2.50 g, 8.67 mmol) and L3 (1.19 g, 3.19 mmol) are added to acetonitrile (100 mL) and reacted at 50° C. overnight. TLC monitoring showed that the bupivacaine is completely reacted and the reaction solution is concentrated to obtain a crude product. The crude product is purified by column chromatography to yield 4.51 g of product Y4. $^1$H NMR: (CDCl$_3$): 0.95-0.99 (m, 3H), 1.23-1.36 (m, 2H), 1.77-2.49 (m, 25H), 3.32-3.38 (m, 4H), 4.03-4.13 (m, 2H), 4.75-4.79 (s, 2H), 5.90-5.94 (m, 1H), 6.87 (s, 2H), 7.04-7.14 (m, 3H), 10.02 (s, 1H).

Example 19 Synthesis of Bupivacaine Conjugate 11 (8-Arm-PEG-Bupivacaine, 20K)

8-arm-PEG-N₃ $\xrightarrow{Y5}$

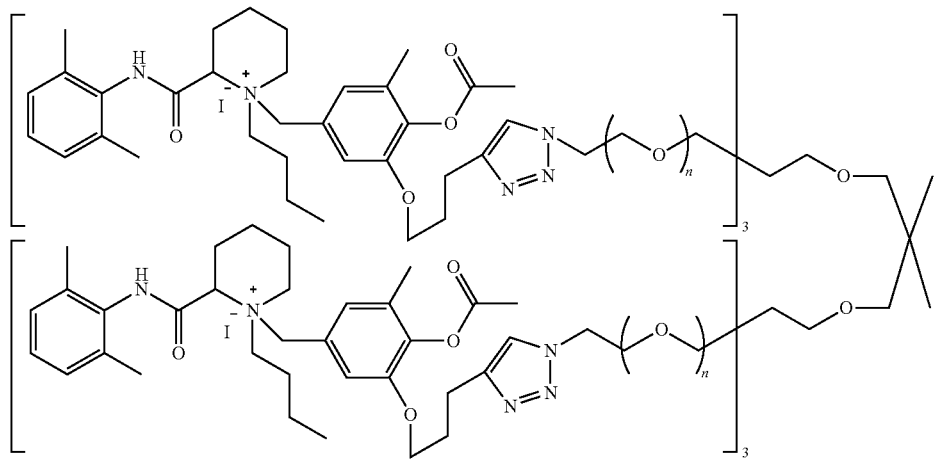

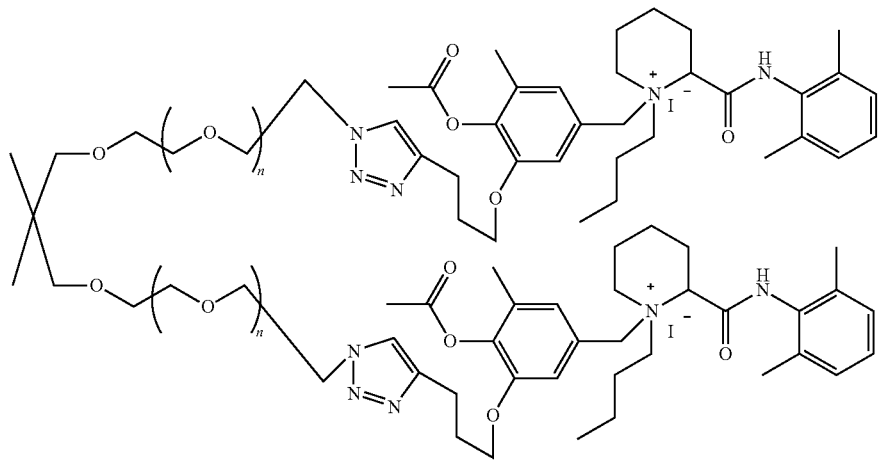

11

8-arm-PEG-N₃ (20K, 2.00 g, 0.10 mmol), the compound Y5 (793 mg, 1.20 mmol), and vitamin C (440 mg, 2.50 mmol) are added to N,N-dimethylformamide (20 mL), and stirred rapidly to make the above materials dissolved. And then an aqueous solution (4.4 mL, 2.2 mL/g PEG) of copper sulfate pentahydrate (250 mg, 1.00 mmol) is added, and the mixture is allowed to react overnight at room temperature, and precipitation is carried out with isopropyl alcohol to obtain 1.60 g of product. ¹H NMR: (CDCl₃): 0.95-0.99 (m, 3H), 1.23-1.36 (m, 2H), 1.77-2.49 (m, 22H), 2.82 (m, 2H), 3.32-3.38 (m, 4H), 3.53 (m, 1800H), 3.87-3.96 (m, 4H), 4.03-4.13 (m, 2H), 4.75-4.79 (s, 2H), 5.90-5.94 (m, 1H), 6.87 (s, 2H), 7.04-7.14 (m, 3H), 10.02 (s, 1H).

Example 20 Synthesis of Linking Chain (L4)

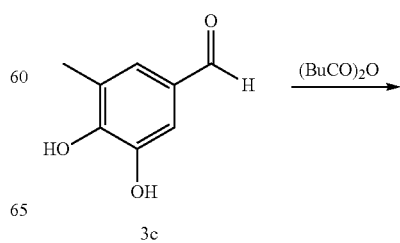

3c

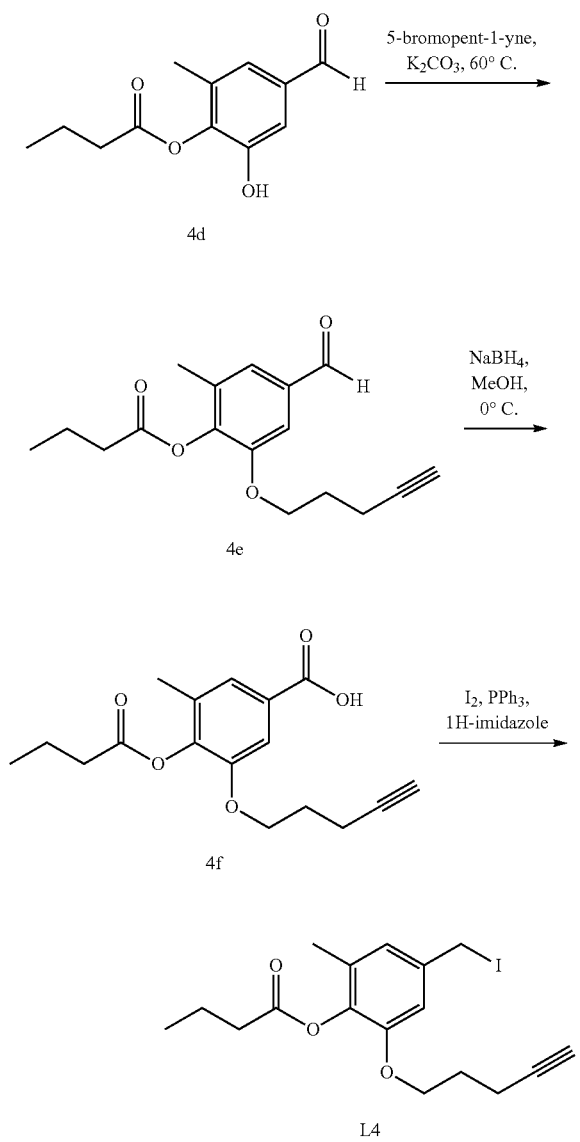

the reaction, the mixture is poured into ice water, and the resulting solution is extracted with diethyl ether. The organic phases are mixed, washed with water, and dried. After concentration, 17.7 g of product 4e is obtained.

4e (17.3 g, 60 mmol) is added to absolute methanol (150 mL), and cooled to 0° C., and then sodium borohydride (1.82 g, 48 mmol) is added. A reaction is carried out at the same temperature for 10 min, and quenched with 1 M HCl. The methanol is rotary-evaporated to dryness. The ethyl acetate and saturated brine are added. And the aqueous phase is extracted with ethyl acetate. The organic phases are mixed, washed with saturated brine and dried. After filtration, the filtrate is concentrated to obtain a crude product. The crude product is purified by column chromatography to yield 11.2 g of product 4f.

Iodine (11.4 g, 45 mmol), triphenylphosphine (11.8 g, 45 mmol) and imidazole (3.06 g, 45 mmol) are added to dichloromethane (90 mL) and stirred at 0° C. for 20 min, a solution of 4f (8.7 g, 30 mmol) in dichloromethane (30 mL) is added, and the mixture is reacted at 0° C. for 30 min. The liquid mixture is washed with 2N hydrochloric acid, a saturated sodium bisulfite solution and brine, dried and evaporated to dryness to obtain a crude product. The crude product is purified by column chromatography to yield 7.8 g of product IA. $^1$H NMR: (DMSO-$d_6$): 0.98 (s, 3H), 1.78 (m, 2H), 2.06 (s, 3H), 2.23 (m, 2H), 2.24-2.31 (m, 5H), 2.81 (m, 1H), 3.90-4.08 (m, 2H), 4.57 (s, 2H), 6.92 (d, 1H), 7.02 (d, 1H).

Example 21 Synthesis of Bupivacaine Quaternary Ammonium Salt (Y6)

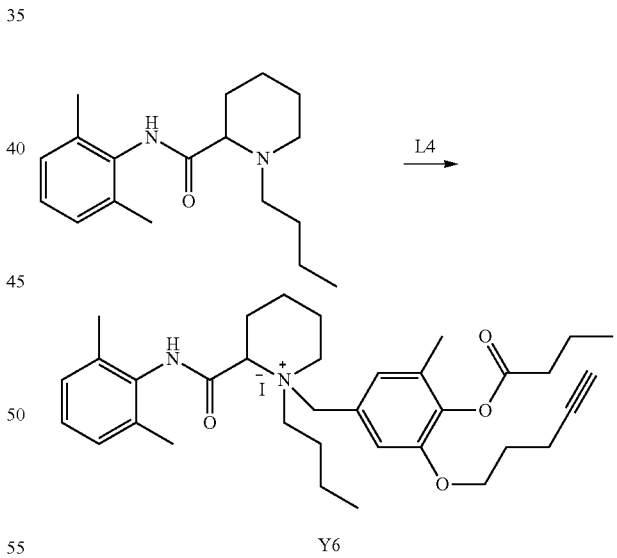

3c (27.5 g, 181 mmol) is added to N,N-dimethylformamide (180 mL), cooled to 0° C., sodium hydride (7.2 g, 181 mmol) is added in batches, and the reaction is carried out for 10 minutes after the addition. After heating to room temperature, butyric anhydride (28.9 g, 183 mmol) is added, and the reaction is carried out for 4 hours after the addition. Ice water and 10% hydrochloric acid are added to the reaction liquid, and the reaction liquid is extracted with ethyl acetate. The organic phases are mixed, washed with a saturated sodium bicarbonate solution, water and saturated brine respectively and dried. After the solution is concentrated, the residue is crystallized with chloroform to yield 21.5 g of product 4d.

4d (20.0 g, 90 mmol) and sodium carbonate (28.6 g, 270 mmol) are added to N,N-dimethylformamide (150 mL), heated to 60° C. for reaction for half an hour, and then cooled to room temperature, 5-bromopent-1-yne (19.8 g, 135 mmol) is added, and the reaction is continued to be carried out at the same temperature. After the completion of Bupivacaine (2.50 g, 8.67 mmol) and L4 (1.28 g, 3.19 mmol) are added to acetonitrile (100 mL) and reacted at 50° C. overnight. TLC monitoring showed that the bupivacaine is completely reacted and the reaction solution is concentrated to obtain a crude product. The crude product is purified by column chromatography to yield 4.82 g of product Y6. $^1$H NMR: (CDCl$_3$): 0.95-0.99 (m, 6H), 1.23-1.36 (m, 4H), 1.77-2.49 (m, 25H), 3.32-3.38 (m, 4H), 4.03-4.13 (m, 2H), 4.75-4.79 (m, 3H), 5.90-5.94 (m, 1H), 6.87 (s, 2H), 7.04-7.14 (m, 3H), 10.02 (s, 1H).

Example 22 Synthesis of Bupivacaine Conjugate 12
(8-Arm-PEG-Bupivacaine, 20K)

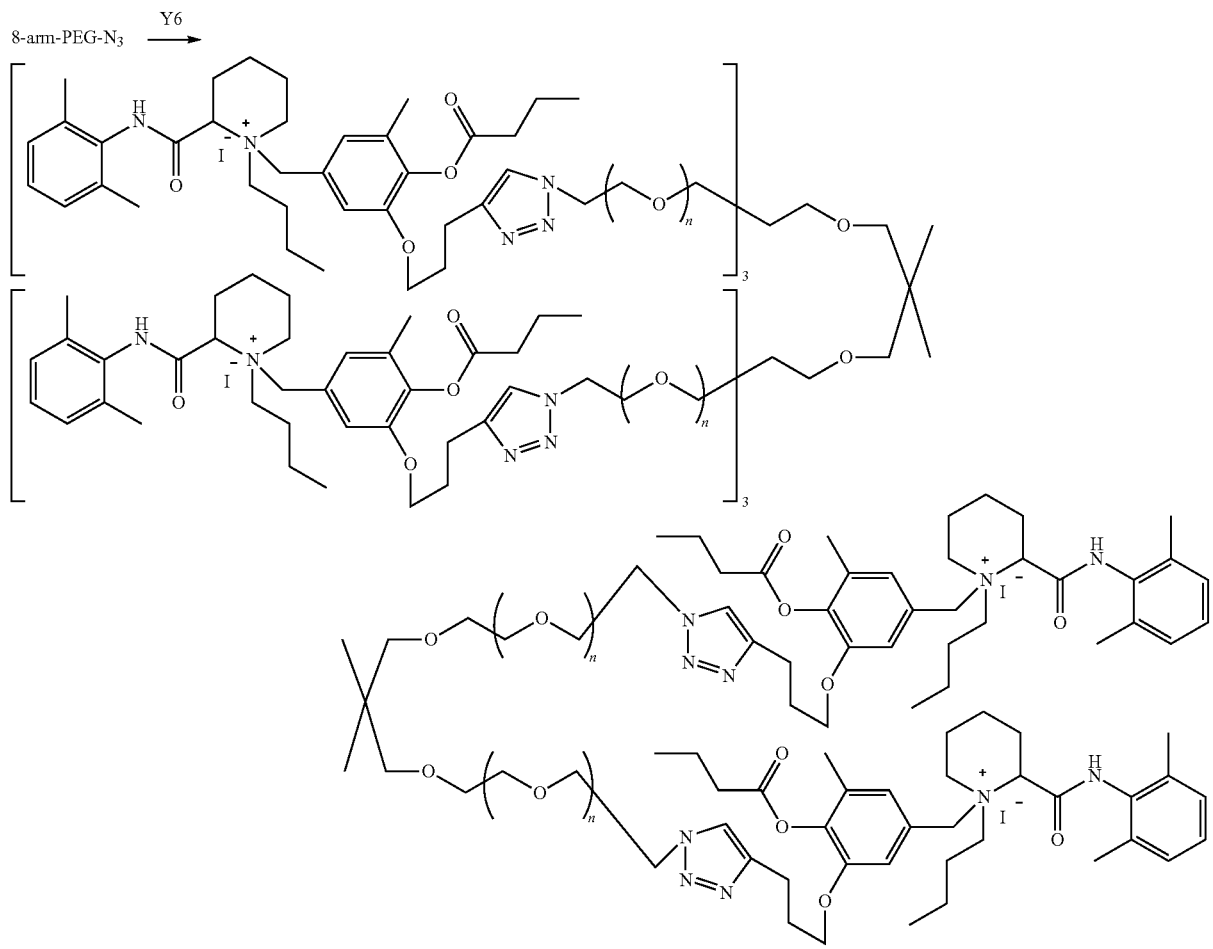

8-arm-PEG-N$_3$ (20K, 2.00 g, 0.10 mmol), the compound Y6 (826 mg, 1.20 mmol), and vitamin C (440 mg, 2.50 mmol) are added to N,N-dimethylformamide (20 mL), and stirred rapidly to make the above materials dissolved. And then an aqueous solution (4.4 mL, 2.2 mL/g PEG) of copper sulfate pentahydrate (250 mg, 1.00 mmol) is added, and the mixture is allowed to react overnight at room temperature, and precipitation is carried out with isopropyl alcohol to obtain 1.72 g of product. $^1$H NMR: (CDCl$_3$): 0.95-0.99 (m, 48H), 1.23-1.36 (m, 32H), 1.77-2.49 (m, 176H), 2.82 (m, 16H), 3.32-3.38 (m, 32H), 3.53 (m, 1800H), 3.87-3.96 (m, 32H), 4.03-4.13 (m, 16H), 4.75-4.79 (m, 16H), 5.90-5.94 (m, 8H), 6.87 (s, 16H), 7.04-7.14 (m, 24H), 10.02 (s, 8H).

Example 23 Bupivacaine Sustained Release Lyophilized Powder Preparation

The main components and mass ratios are as follows:

| | |
|---|---|
| Bupivacaine hydrochloride | 8 parts |
| Hydrogenated soybean lecithin | 6-6.5 parts |

-continued

| | |
|---|---|
| Cholesterol | 3 parts |
| Glycerol trilaurate | 0.1-0.2 part |

Hydrogenated soybean lecithin, cholesterol, and glycerol trilaurate are dissolved in chloroform as a lipid phase;

Bupivacaine hydrochloride is dissolved in water as an aqueous phase;

The aqueous phase is added to the lipid phase and shearing is carried out at a high speed to form a water-in-oil emulsion;

The solvent is removed, and filtering, washing, and lyophilizing are carried out to obtain a liposomal lyophilized powder preparation of bupivacaine.

Example 24 In Situ Lipid Gel Preparation of Bupivacaine

The main ingredients and dosage are as follows:

| | |
|---|---|
| Bupivacaine hydrochloride | 50 mg/g the total weight of preparation |
| Soybean Lecithin | 40 ml |
| Absolute ethanol | 20 ml |
| Water for injection | 30 ml |

The above ingredients are mixed, placed in a sealed container, heated under magnetic stirring, fully dissolved, and cooled to obtain an in situ lipid gel preparation of bupivacaine.

Example 25 Sustained Release Tablets of Bupivacaine

The main ingredients and dosage are as follows:

| | |
|---|---|
| Bupivacaine hydrochloride | 5 mg |
| Hydroxypropyl methylcellulose | 50 mg |
| Lactose | 20 mg |
| Magnesium stearate | 10 mg |
| Microcrystalline cellulose | 30 mg |

Bupivacaine hydrochloride is mixed with microcrystalline cellulose, and hydroxypropyl methylcellulose, and lactose are added and the materials are mixed uniformly, the mixture is dissolved in ethanol to be wetted to make a soft material, the soft material is granulated, the granulated material is dried, granule dispersion is carried out, and magnesium stearate is added, the materials are mixed uniformly, and the mixture is tableted to obtain skeleton-dispersed sustained-release tablets of bupivacaine.

Example 26 Sustained Release Tablets of Bupivacaine

The main ingredients and dosage are as follows:

| | |
|---|---|
| Cores of the tablets: | |
| Bupivacaine hydrochloride | 5 mg |
| Lactose | 40 mg |
| Ethyl cellulose | 10 mg |
| Magnesium stearate | 20 mg |
| Coating solution: | |
| Cellulose acetate | 30 mg |
| PEG 400 | 15 ml |
| Acetone | 100 ml |

Bupivacaine hydrochloride is uniformly mixed with lactose, ethyl cellulose in ethanol is added, so that a soft material is made, the soft material is sieved, wet granules are made, dried, and sieved, and magnesium stearate is added, the materials are mixed uniformly and the mixture is tableted. An acetone aqueous solution containing PEG 400 and cellulose acetate is used for spray-coating, and drying, and laser drilling are carried out to obtain membrane-controlled sustained-release tablets of bupivacaine.

Example 27 Bupivacaine Sustained Release Pills

The main ingredients and dosage are as follows:

| | |
|---|---|
| Cores of the pills: | |
| Bupivacaine hydrochloride | 80 mg |
| Starch | 40 mg |
| Dextrin | 45 mg |
| Coating solution: | |
| Acrylic resin No. II | 1.5 g |
| PEG 400 | 3 ml |
| Diethyl phthalate | 0.01 g |
| Talc powder | moderate amount |
| Ethanol | adding up to 25 ml |

The bupivacaine hydrochloride is thoroughly and uniformly mixed with starch and dextrin, and the pellet core is made in a coating pot with a certain concentration of ethanol, taken out, and dried. After the fine powder is removed, the dried pellet core is weighed, and put in the coating pot to be coated to obtain bupivacaine sustained-release pellets. It can be further processed into other dosage forms.

Example 28 Bupivacaine Analgesic Minimum and Maximum Dose (or Minimum Anesthetic Dose) Test 1. Experimental Materials 1.1 Experimental animals: SD rats, SPF grade, male, 6-9 weeks old, 200-260 g, purchased from Shanghai Slack Laboratory Animals Co., Ltd., experimental animal certificate number: 2015000527734.

1.2 Experimental animal feeding conditions: The animal room environment is maintained at a temperature of 23±2° C., and a humidity of 40-70%, alternating 12 hours of light and dark. Experimental animals are acclimated for at least 7 days prior to the experiment.

1.3 Test substance: bupivacaine injection, diluted with physiological saline to the target concentration; the reference substance is physiological saline.

2. Experimental Method 2.1 Catheterization Around the Sciatic Nerve:

After the animals are anesthetized by intraperitoneal injection of 10% chloral hydrate solution, the sciatic nerve is exposed to the biceps and gluteus maximus joints of the hind limbs through surgery, and silicone flexible catheters of the same length (7 cm) are placed around the sciatic nerve. the other ends of the catheters are subcutaneously embedded in the back of the rat, and then sutured and fixed, and 0.2 mL of an antibiotic solution (5,000 U/ml penicillin G) is injected for anti-inflammatory.

2.2 Screening of Animals:

After 2-3 days of catheterization, the SD rats with the body weight of 230-250 g and into which catheters are embedded are screened before the experiment by a hot plate method. The hot plate is heated to (56±1)° C., one of the hind paws of the rat is placed on the hot plate, and the other hind paw is placed in the laboratory room temperature condition, and the tested paw withdrawal time is observed and recorded. The average value of three times measured is recorded as a basic pain threshold. If the measurement result of the paw withdrawal time exceeds 5.0 seconds, the basic pain threshold of the rat does not meet the requirements and should be excluded.

2.3 Grouping and Administration:

Twenty-four qualified rats (animals with no dyskinesia and pain threshold change after catheterization) are randomly divided into 6 groups, 4 rats in each group, the first group is a control group, the experimental animals are administered with normal saline, and the other groups are administered with different doses of bupivacaine injection. The grouping information is shown in Table 1. Each group is injected with a corresponding drug through the catheter around the sciatic nerve.

TABLE 1

Experimental animal grouping and drug administration information

| groups | Animal numbers | drugs | doses (mg/kg) | Actual doses mg/rat | Administration volume ml/rat | Administration mode |
|---|---|---|---|---|---|---|
| 1 | 4 | Vehicle | — | — | 0.4 | trans-catheter |
| 2 | 4 | Bupivacaine injection group | 3 | 0.66 | 0.4 | trans-catheter |
| 3 | 4 | Bupivacaine injection group | 1 | 0.22 | 0.4 | trans-catheter |
| 4 | 4 | Bupivacaine injection group | 0.3 | 0.066 | 0.4 | trans-catheter |
| 5 | 4 | Bupivacaine injection group | 0.1 | 0.022 | 0.4 | trans-catheter |
| 6 | 4 | Bupivacaine injection group | 0.03 | 0.0066 | 0.4 | trans-catheter |

*The dose is based on the actual experiment; the administration dose is determined according to the average body weight of the experimental animals. The administration concentration and volume of the animals in the single dose group are the same, for example, the animal average animal weight is 220 g, and the administration dose is 1 mg/kg, and the administration concentrations are determined to be 0.66 mg/ml, 0.4 ml/per rat.

2.4 Sensory Block (Hot Plate Paw Withdrawal Time):

The sensory block of the rats is examined by a hot plate method. The hot plate is heated to $(56 \pm 1)°$ C., one of the hind paws of the rat is placed on the hot plate, and the other hind paw is placed at room temperature in the laboratory, the tested paw withdrawal time is observed and recorded. The average value of two to three times is recorded as a pain threshold. The paw withdrawal time of the hot plate method is recorded. In order to avoid the damage of the experimental animal body, if the rat has not withdrawal paw in the hot plate experiment for more than 15 s, the rat should be removed from the hot plate, and the experimental result is recorded as 15 s. The time point for determining the paw withdrawal time of the hot plate is before administration, and 5 minutes, 10 minutes, 30 minutes, 1 hour, and 2 hours after administration.

2.5 Motor Block (Four-Level Score):

The exercise condition of each group of rats is evaluated by a motor block four-level scoring method. The scoring criteria are: paws can be dorsiflexed, stretched, valgus and other normal exercises, scored by 1 point; paws can be dorsiflexed, bendable or after the adduction, although the paws can be stretched, the stretching ability is weakened, scored by 2 points; the paws can perform dorsiflexion, but no longer has the ability to stretch, scored by 3 points; the paws completely lose the ability of dorsiflexion, curling and stretching, and the rats produce a gait defect, scored by 4 points. The time point for measuring the motor block score is before administration, and 5 min, 10 min, 30 min, 1 h, and 2 h after administration.

All clinical symptoms of each animal should be recorded at the beginning of the experiment and during the experiment, and observation should be performed at the same time every day.

3. Experimental Result 3.1 Clinical Symptoms

In the experiment, no obvious clinical abnormal symptoms are observed in all groups of animals.

3.2 Effect of Different Doses of Bupivacaine Injection on the Hot Plate Paw Withdrawal Time of SD Rats The effect of different doses of bupivacaine injection on the hot plate paw withdrawal time of SD rats is shown in Table 2. From the data in Table 2, it can be seen:

In the absence of administration, there is no significant difference in the hot plate paw withdrawal time between the experimental SD rats in each group ($p>0.05$).

After transcatheter administration, compared with the vehicle group, the hot plate paw withdrawal time of experimental SD rats in different doses of bupivacaine injection group has different changes. Compared with the vehicle group, the hot plate paw withdrawal time of the experimental SD rats in the group of bupivacaine injection of 0.66 mg/rat is significantly higher than that of the vehicle group at the 5, 10, 30, 60, and 120 min time points ($p<0.05$); the hot plate paw withdrawal time of the experimental SD rats in the group of bupivacaine injection of 0.22 mg/rat is significantly higher than that of the vehicle group at the 30 and 60 min time points ($p<0.05$); the hot plate paw withdrawal time of the experimental SD rats in the group of bupivacaine injection of 0.066 mg/rat is significantly higher than that of the vehicle group at the 5, 10, 30, 60, and 120 min time points ($p<0.05$); the hot plate paw withdrawal time of the experimental SD rats in the group of bupivacaine injection of 0.022 mg/rat is significantly higher than that of the vehicle group at the 60 min time points ($p<0.05$); and the hot plate paw withdrawal time of the experimental SD rats in the group of bupivacaine injection of 0.00066 mg/rat is significantly higher than that of the vehicle group at the 5 and 60 min time points ($p<0.05$).

After the solvent control group is administered with normal saline, the reduction of the hot plate paw withdrawal time of the animals is observed. According to the analysis, it may be due to the osmotic pressure and temperature of the normal saline, which causes the local stimulation to play a certain effect on the algesthesia.

TABLE 2

Effect of different doses of bupivacaine injection on the hot plate paw withdrawal time of SD rats

| Groups | 0 min | 5 min | 10 min | 30 min | 60 min | 120 min |
|---|---|---|---|---|---|---|
| 1 | 2.75 ± 1.49 | 1.55 ± 1.11 | 2.27 ± 1.46 | 1.52 ± 0.7 | 1.42 ± 0.53 | 1.65 ± 1.13 |
| 2 | 3.26 ± 0.88 | 6.32 ± 2.29* | 7.7 ± 3.88* | 7.85 ± 3.36* | 5.91 ± 1.9* | 4.26 ± 1.42* |
| 3 | 2.75 ± 0.74 | 5.17 ± 5.41 | 7.13 ± 5.43 | 7.13 ± 4.01* | 3.24 ± 0.85* | 2.13 ± 0.8 |

TABLE 2-continued

Effect of different doses of bupivacaine injection on the hot plate paw withdrawal time of SD rats

| Groups | 0 min | 5 min | 10 min | 30 min | 60 min | 120 min |
|---|---|---|---|---|---|---|
| 4 | 3.42 ± 0.87 | 6.08 ± 1.68* | 7.11 ± 2.55* | 7.09 ± 1.45* | 3.62 ± 1.25* | 3.76 ± 0.69* |
| 5 | 3.08 ± 0.61 | 4.41 ± 3.24 | 4.22 ± 2.45 | 3.59 ± 1.89 | 2.63 ± 0.41* | 2.96 ± 1.38 |
| 6 | 3.06 ± 1.1 | 3.36 ± 0.91* | 2.67 ± 0.6 | 3.11 ± 1.22 | 2.66 ± 0.53* | 3.09 ± 0.82 |

Results are expressed as mean ± SD, *p <0.05.

3.3 Effects of Different Doses of Bupivacaine Injection on Motor Function Scores of SD Rats The effect of different doses of bupivacaine injection on the motor function score of SD rats is shown in Table 3. From the data in Table 3, it can be seen:

There is no significant difference in motor function scores between the experimental SD rats in each group without drug administration.

After transcatheter administration, compared with the vehicle group, the motor function score of the experimental SD rats in the group of bupivacaine injection of 0.66 mg/rat is significantly higher than that of the vehicle group at the 10, 30, and 60 min time points (p<0.05). The group of bupivacaine injection of 0.22 mg/rat is higher than the control group, but there is no statistical difference (p>0.05); the motor function scores of the experimental SD rats in the other dose groups are the same as those in the control group.

TABLE 3

Effect of different doses of bupivacaine injection on motor function scores of SD rats

| Groups | 0 min | 5 min | 10 min | 30 min | 60 min | 120 min |
|---|---|---|---|---|---|---|
| 1 | 1 ± 0 | 1 ± 0 | 1 ± 0 | 1 ± 0 | 1 ± 0 | 1 ± 0 |
| 2 | 1 ± 0 | 1 ± 0 | 1.75 ± 0.5* | 1.75 ± 0.5* | 1.75 ± 0.5* | 1 ± 0 |
| 3 | 1 ± 0 | 1.5 ± 0.58 | 1.5 ± 0.58 | 1.25 ± 0.5 | 1 ± 0 | 1 ± 0 |
| 4 | 1 ± 0 | 1 ± 0 | 1 ± 0 | 1 ± 0 | 1 ± 0 | 1 ± 0 |
| 5 | 1 ± 0 | 1 ± 0 | 1 ± 0 | 1 ± 0 | 1 ± 0 | 1 ± 0 |
| 6 | 1 ± 0 | 1 ± 0 | 1 ± 0 | 1 ± 0 | 1 ± 0 | 1 ± 0 |

Results are expressed as mean ± SD, *p <0.05.

Bupivacaine injection showed a motor block effect and a hot plate analgesic effect at a dose of 3 mg/kg (0.66 mg/rat) and 1 mg/kg (0.22 mg/rat). Bupivacaine injection showed a hot plate analgesic effect at doses of 0.3, 0.1, 0.03 mg/kg (ie, 0.066, 0.022, 0.066 mg/rat), but no motor nerve block effect is observed, i.e. a non-anesthetic analgesic effect is achieved.

Example 29 PEG-Bupivacaine Conjugate Hydrolysis Drug Release Experiment

Preparation of isotonic phosphate buffer (0.01 mol/L, pH 7.4, PBS): 8.0 g of NaCl, 0.2 g of $KH_2PO_4$, 2.9 g of $Na_2HPO_4 \cdot 12H_2O$ and 0.2 g of KCl are added sequentially to a quantitative container, and an appropriate amount of distilled water is added to dissolve, and then the volume is adjusted to 1000 mL and the obtained buffer is stored in a refrigerator at 4° C. for use.

Hydrolysis drug release for the PEG-bupivacaine conjugate: PEG-bupivacaine products (bupivacaine conjugate 6, prepared in Example 9 of the present invention; bupivacaine conjugate 10, prepared in Example 16 of the present invention) are dissolved in PBS buffer at about 2 mg/mL and placed in a water-bathing constant temperature vibrator at 37° C. Samples are taken at 0 h, 6 h, 12 h, 24 h, 48 h, 72 h, 96 h, 120 h and 144 h, and the content of free bupivacaine is determined by HPLC.

The experimental results are shown in Table 4. As can be seen from the data in Table 4, the hydrolysis half-life of the bupivacaine conjugate 6 is about 22 h, the hydrolysis half-life of the bupivacaine conjugate 10 is about 35 h, and the bupivacaine conjugate 10 is more stable than the bupivacaine conjugate 6. Both PEG-bupivacaine products can slowly release free bupivacaine.

TABLE 4

Hydrolysis drug release rate of PEG-bupivacaine in pH 7.4 buffer

| | PEG-bupivacaine hydrolysis rate(%) | |
|---|---|---|
| Time (h) | bupivacaine conjugate 6 | bupivacaine conjugate 10 |
| 0 | 0.57 | 0.43 |
| 6 | 18.58 | 15.03 |
| 12 | 33.21 | 25.19 |
| 24 | 52.85 | 40.37 |
| 48 | 76.36 | 61.72 |
| 72 | 87.12 | 76.25 |
| 96 | 92.89 | 87.28 |
| 120 | 95.02 | 92.76 |
| 144 | 95.21 | 96.13 |

Example 30 Study of Non-Anesthetic Analgesic Effect of PEG-bupivacaine Conjugate Male Sprague-Dawley rats are used in the study, about 230-250 g when accepted, and acclimated for at least 7 days prior to the experiment. Two rats are raised in each cage and fed freely with feed and water. The environmental conditions of the breeding room are 23±2° C., and the relative humidity is 40% to 70%, alternating 12 hours of light and dark. SD rats with basic pain thresholds that do not meet the requirements are excluded through screening by a hot plate method before the experiment. The qualified rats are randomly divided into 4 groups, 4 rats in each group, which are labeled as groups G1, G2, G3, and G4, respectively. Administration by direct injection in the sciatic nerve is adopted, and with the rat's back facing up, the drug is injected around the right sciatic nerve trunk between the right hip and the right thigh. The grouping information of the experimental animals is shown in Table 5.

TABLE 5

Experimental animal grouping and drug administration information

| Groups | Animal numbers | Drugs | Dose (mg/kg)[a] | Administration volume ml/rat | Administration mode |
|---|---|---|---|---|---|
| G1 | 4 | Vehicle | — | 0.4 | Direct injection |
| G2 | 4 | bupivacaine conjugate 10 | 32 | 0.4 | Direct injection |

The experimental results are shown in Table 6. As can be seen from the data in Table 6, there is no significant difference in the hot plate paw withdrawal time of SD rats in each experimental group in the absence of administration. After direct injection for administration, the hot plate paw withdrawal time of the SD rats in the experimental group of two different structures of PEG-bupivacaine and the vehicle group both are changed. The hot plate paw withdrawal time of SD rats in the group of the bupivacaine conjugate 10 of 32 mg/kg is significantly higher than that of the vehicle group at 0.5 h, 1 h, 2 h, 3 h, 4 h and 8 h after administration; the hot plate paw withdrawal time of SD rats in the group of the bupivacaine conjugate 11 of 24 mg/kg is significantly higher than that of the vehicle group within 6 h after administration; the hot plate paw withdrawal time of SD rats in the group of the bupivacaine conjugate 12 of 48 mg/kg is significantly higher than that of the vehicle group within 2 h after administration.

TABLE 6

Effect of PEG-bupivacaine conjugate on the hot plate paw withdrawal time of SD rats

| Groups | Drugs | Dose (mg/kg) | 0.5 h | 1 h | 2 h | 4 h | 6 h | 8 h | 10 h | 12 h | 24 h |
|---|---|---|---|---|---|---|---|---|---|---|---|
| G1 | Vehicle | — | 2.68 | 3.51 | 3.83 | 2.63 | 3.64 | 2.66 | 2.61 | 2.34 | 2.21 |
| G2 | bupivacaine conjugate 10 | 32 | 11.85 | 11.98 | 8.91 | 10.74 | 11.92 | 8.49 | 6.64 | 3.82 | 3.81 |
| G3 | bupivacaine conjugate 11 | 24 | 9.60 | 9.99 | 5.02 | 6.65 | 6.44 | 3.69 | 3.24 | 2.62 | 3.77 |
| G4 | bupivacaine conjugate 12 | 48 | 6.49 | 6.77 | 3.52 | 4.82 | 4.59 | 4.34 | 4.30 | 2.80 | 3.25 |

TABLE 5-continued

Experimental animal grouping and drug administration information

| Groups | Animal numbers | Drugs | Dose (mg/kg)[a] | Administration volume ml/rat | Administration mode |
|---|---|---|---|---|---|
| G3 | 4 | bupivacaine conjugate 11 | 24 | 0.4 | Direct injection |
| G4 | 4 | bupivacaine conjugate 12 | 48 | 0.4 | Direct injection |

Note:
[a]The dose shown refers to the dose of PEG-bupivacaine converted to bupivacaine according to the drug loading amount.

The bupivacaine conjugates 10, 11 and 12 are the products prepared in the examples 16, 19 and 22 of the invention, respectively.

Sensory block (hot plate paw withdrawal time): The sensory block of the rat is examined by a hot plate method, and the hot plate is heated to (56±1)° C., and one of the hind paws of the rat is placed on the hot plate. The other hind paw is in the laboratory room temperature condition, and the tested paw withdrawal time is observed and recorded. The average value of two to three times measured is recorded as a pain threshold. In order to avoid the damage of the experimental animal body, if the rat has no paw withdrawal in the hot plate experiment for more than 15 s, the rat should be removed from the hot plate, and the experimental result is recorded as 15 s. The time point for determining the paw withdrawal time of the hot plate is before administration, and 0.5 h, 1 h, 2 h, 4 h, 6 h, 8 h, 10 h, 12 h, and 24 h after administration.

Motor block (four-level score): The exercise condition of each group of rats is evaluated by the motor block four-level scoring method. The scoring criteria are: paws can be dorsiflexed, stretched, valgus and other normal exercises, scored by 1 point; paws can be dorsiflexed, bendable or after the adduction, although the paws can be stretched after the adduction, the stretching ability is weakened, scored by 2 points; the paw can perform dorsiflexion, but no longer has the ability to stretch, scored by 3 points; the paws completely lose the ability of dorsiflexion, curling and stretching, and the rats produce a gait defect, scored by 4 points. The time point for measuring the motor block score is before administration, and 0.5 h, 1 h, 2 h, 4 h, 6 h, 8 h, 12 h, and 24 h after administration.

The experimental results are shown in Table 7. From the data in Table 7, it is found that there is no significant difference in motor function scores of SD rats in each experimental group in the absence of administration. After the direct injection for administration, the motor scores of bupivacaine conjugates 10, 11 and 12 at different time points are not significantly different from those of the vehicle group.

From the results of sensory block and motor block, the bupivacaine conjugate 10 does not affect the motor function of SD rats when administered at 32 mg/kg, and the analgesic effect could reach 8 h; the bupivacaine conjugate 11 does not affect the motor function of SD rats when administered at 24 mg/kg, and the analgesic effect could reach 6 h.

TABLE 7

Effect of PEG-bupivacaine conjugate on motor function score of SD rats

| Groups | Drugs | Dose (mg/kg) | 0 h | 0.5 h | 1 h | 2 h | 4 h | 6 h | 8 h | 12 h | 24 h |
|---|---|---|---|---|---|---|---|---|---|---|---|
| G1 | Vehicle | — | 1 ± 0 | 1 ± 0 | 1 ± 0 | 1 ± 0 | 1 ± 0 | 1 ± 0 | 1 ± 0 | 1 ± 0 | 1 ± 0 |
| G2 | bupivacaine conjugate 10 | 32 | 1 ± 0 | 1 ± 0 | 1.75 ± 0.5 | 1.75 ± 0.5 | 1.75 ± 0.5 | 1.75 ± 0.5 | 1.75 ± 0.5 | 1 ± 0 | 1 ± 0 |
| G3 | bupivacaine conjugate 11 | 24 | 1 ± 0 | 1 ± 0 | 1 ± 0 | 1 ± 0 | 1 ± 0 | 1 ± 0 | 1 ± 0 | 1 ± 0 | 1 ± 0 |
| G4 | bupivacaine conjugate 12 | 48 | 1 ± 0 | 1 ± 0 | 1 ± 0 | 1 ± 0 | 1 ± 0 | 1 ± 0 | 1 ± 0 | 1 ± 0 | 1 ± 0 |

Example 31 Study of Analgesic Effect of PEG-bupivacaine Conjugate on Rat Plantar Incision After SD rats inhale anesthesia (isoflurane), an incision of about 1 cm in length from the proximal end of the pelma to the toe is made: after the skin and fascia are cut, the plantar muscle is picked up with an ophthalmic forceps and cut longitudinally (maintaining the starting and ending point and attachment of muscles); pressing is carried out for hemostasis, physiological saline and test drugs are injected into the muscles of animal's legs, and then the pain threshold detection is performed by the hot plate method. Within 24 hours after the model is successful, the rats develop significant hyperalgesia. Qualified rats are randomly divided into 5 groups, 6 rats in each group, which are labeled as groups G1, G2, G3, G4 and G5, respectively. The plantar subcutaneous injection method for administration is used, and the grouping information of the experimental animals is shown in Table 8.

TABLE 8

Experimental animal grouping and drug administration information

| Groups | Animal numbers | Drugs | Dose (mg/kg)[a] | Administration volume ml/rat |
|---|---|---|---|---|
| G1 | 6 | Vehicle | — | 0.4 |
| G2 | 6 | bupivacaine | 8 | 0.4 |
| G3 | 6 | bupivacaine conjugate 10 | 32 | 0.4 |
| G4 | 6 | bupivacaine conjugate 11 | 24 | 0.4 |
| G5 | 6 | bupivacaine conjugate 12 | 48 | 0.4 |

Note:
[a]The dose shown refers to the dose of PEG-bupivacaine converted to bupivacaine according to the drug loading amount.

Sensory block (hot plate paw withdrawal time): The sensory block of the rat is examined by a hot plate method, and the hot plate is heated to $(56\pm1)°$ C., and one of the hind paws of the rat is placed on the hot plate, the other hind paw is in the laboratory room temperature condition, and the tested paw withdrawal time is observed and recorded. The average value of two to three times measured is recorded as a pain threshold. In order to avoid the damage of the experimental animal body, if the rat has no paw withdrawal in the hot plate experiment for more than 15 s, the paws should be removed from the hot plate, and the experimental result is recorded as 15 s. The time point for determining the paw withdrawal time of the hot plate is before administration, and 0.5 h, 1 h, 2 h, 4 h, 6 h, 8 h, 12 h, and 24 h after administration.

The experimental results are shown in Table 9. As can be seen from the data in Table 9, there is no significant difference in the hot plate paw withdrawal time of SD rats in each experimental group in the absence of administration. After direct injection for administration, the hot plate paw withdrawal time of the SD rats in the experimental group of three different structures of PEG-bupivacaine and the vehicle group both are changed. The plantar incision model reduces the hot plate paw withdrawal time of the rats from 5.79 s before surgery to 1.23 s after surgery. The hot plate paw withdrawal time of SD rats with bupivacaine injection of 8 mg/kg is significantly higher than that of the vehicle group only at 0.5 h and 1 h after administration; the hot plate paw withdrawal time of SD rats with bupivacaine conjugate 10 injection of 32 mg/kg is significantly higher than that of the vehicle group at 0.5 h, 1 h, 2 h, 4 h, 6 h and 8 h after administration; the hot plate paw withdrawal time of SD rats with bupivacaine conjugate 11 injection of 24 mg/kg is significantly higher than that of the vehicle group within 6 h after administration; the hot plate paw withdrawal time of SD rats with bupivacaine conjugate 12 injection of 48 mg/kg is significantly higher than that of the vehicle group within 2 h after administration.

TABLE 9

Effect of PEG-bupivacaine conjugate on the hot plate paw withdrawal time of SD rats

| Groups | Drugs | Dose (mg/kg) | Base value before surgery | 0 h | 0.5 h | 1 h | 2 h | 4 h | 6 h | 8 h | 12 h | 24 h |
|---|---|---|---|---|---|---|---|---|---|---|---|---|
| G1 | Vehicle | — | 5.79 | 1.23 | 1.20 | 0.99 | 1.14 | 1.67 | 2.10 | 1.32 | 2.43 | 2.10 |
| G2 | bupivacaine | 8 | 4.70 | 1.02 | 7.21 | 6.91 | 1.30 | 1.51 | 1.32 | 2.41 | 1.41 | 1.45 |
| G3 | bupivacaine conjugate 10 | 32 | 5.20 | 1.41 | 6.52 | 7.91 | 6.21 | 6.79 | 7.42 | 7.43 | 2.10 | 1.32 |
| G4 | bupivacaine conjugate 11 | 24 | 4.97 | 1.26 | 7.43 | 8.49 | 9.10 | 7.91 | 8.65 | 2.19 | 1.89 | 1.56 |
| G5 | bupivacaine conjugate 12 | 48 | 5.81 | 1.89 | 8.13 | 7.21 | 6.12 | 2.49 | 2.34 | 2.10 | 1.92 | 1.76 |

Motor block (four-level score): The exercise condition of each group of rats is evaluated by the motor block four-level scoring method. The scoring criteria are: paws can be dorsiflexed, stretched, valgus and other normal exercises, scored by 1 point; paws can be dorsiflexed, bendable or after the adduction, although the paws can be stretched, the stretching ability is weakened, scored by 2 points; the paws can perform dorsiflexion, but no longer has the ability to stretch, scored by 3 points; the paws completely lose the ability of dorsiflexion, curling and stretching, and the rats produce a gait defect, scored by 4 points. The time point for measuring the motor block score is before administration, and 0.5 h, 1 h, 2 h, 4 h, 6 h, 8 h, 12 h, and 24 h after administration.

The experimental results are shown in Table 10. From the data in Table 10, there is no significant difference in motor function scores of SD rats in each experimental group in the absence of administration. After direct injection for administration, from the results of sensory block and motor block, the bupivacaine conjugate 10 does not affect the motor function of SD rats when administered at 32 mg/kg, and the analgesic effect can reach 8 h; the bupivacaine conjugate 11 does not affect the motor function of SD rats when administered at 24 mg/kg, and the analgesic effect can reach 6 h or above; the bupivacaine conjugate 12 does not affect the motor function of SD rats when administered at 48 mg/kg, and the analgesic effect can reach 2 h.

TABLE 11

Experimental animal grouping and drug administration information

| Groups | Animal numbers | Drugs | Dose (mg/kg)$^a$ | Administration volume ml/rat |
|---|---|---|---|---|
| G1 | 6 | Vehicle | — | 0.4 |
| G2 | 6 | bupivacaine | 8 | 0.4 |
| G3 | 6 | bupivacaine conjugate 10 | 32 | 0.4 |
| G4 | 6 | bupivacaine conjugate 11 | 24 | 0.4 |
| G5 | 6 | bupivacaine conjugate 12 | 48 | 0.4 |

Note:
$^a$The dose shown refers to the dose of PEG-bupivacaine converted to bupivacaine according to the drug loading amount.

Sensory block (hot plate paw withdrawal time): The sensory block of the rat is examined by a hot plate method, and the hot plate is heated to $(56\pm1)°$ C., and one of the hind paws of the rat is placed on the hot plate, the other hind paw is in the laboratory room temperature condition, and the tested paw withdrawal time is observed and recorded. The average value of two to three times measured is recorded as a pain threshold. In order to avoid the damage of the experimental animal body, if the rat has no paw withdrawal

TABLE 10

Effect of PEG-bupivacaine conjugate on motor function score of SD rats

| Groups | Drugs | Dose (mg/kg) | 0 h | 0.5 h | 1 h | 2 h | 4 h | 6 h | 8 h | 12 h | 24 h |
|---|---|---|---|---|---|---|---|---|---|---|---|
| G1 | Vehicle | — | 1 ± 0 | 1 ± 0 | 1 ± 0 | 1 ± 0 | 1 ± 0 | 1 ± 0 | 1 ± 0 | 1 ± 0 | 1 ± 0 |
| G2 | bupivacaine | 8 | 1 ± 0 | 1 ± 0 | 1.75 ± 0.5 | 1.75 ± 0.5 | 1.75 ± 0.5 | 1.75 ± 0.5 | 1.75 ± 0.5 | 1 ± 0 | 1 ± 0 |
| G3 | bupivacaine conjugate 10 | 32 | 1 ± 0 | 1 ± 0 | 1.75 ± 0.5 | 1.75 ± 0.5 | 1.75 ± 0.5 | 1.75 ± 0.5 | 1.75 ± 0.5 | 1 ± 0 | 1 ± 0 |
| G4 | bupivacaine conjugate 11 | 24 | 1 ± 0 | 1 ± 0 | 1 ± 0 | 1 ± 0 | 1 ± 0 | 1 ± 0 | 1 ± 0 | 1 ± 0 | 1 ± 0 |
| G5 | bupivacaine conjugate 12 | 48 | 1 ± 0 | 1 ± 0 | 1 ± 0 | 1 ± 0 | 1 ± 0 | 1 ± 0 | 1 ± 0 | 1 ± 0 | 1 ± 0 |

Example 32 Study of Analgesic Effect of PEG-Bupivacaine Conjugate on Rat Sciatica Model Intervertebral disc compression (SNL): This model is a pathological form that simulates clinical disc herniation. The specific method is to remove the autogenous caudal intervertebral disc tissue (annulus fibrosus and nucleus pulposus) form the rats and place the caudal intervertebral disc tissue between the proximal nerve root of the L5 dorsal root ganglion and the lower vertebral body to directly compress the L5 nerve root, wherein damage to the L5 nerve root or dorsal root ganglion should be avoided during the operation. 3 to 15 days after the model is successful, rats develop significant hyperalgesia, so the administration time we chose is between 3 days and 15 days.

Qualified rats are randomly divided into 5 groups, 6 rats in each group, which are labeled as groups G1, G2, G3, G4 and G5, respectively. Administration by intramuscular injection around sciatic nerve is adopted, and the grouping information of the experimental animals is shown in Table 11.

in the hot plate experiment for more than 15 s, the paws should be removed from the hot plate, and the experimental result is recorded as 15 s. The time point for determining the withdrawal time of the hot plate is before administration, and 0.5 h, 1 h, 2 h, 4 h, 6 h, 8 h, 12 h, and 24 h after administration.

The experimental results are shown in Table 12. As can be seen from the data in Table 12, there is no significant difference in the hot plate paw withdrawal time of SD rats in each experimental group in the absence of administration. After direct injection for administration, the hot plate paw withdrawal time of the SD rats in the experimental group of three different structures of PEG-bupivacaine and the vehicle group is changed. SNL causes significant hyperalgesia in rats. The hot plate paw withdrawal time is reduced from 5.19 s before surgery to 1.92 s after surgery. The hot plate paw withdrawal time of SD rats with bupivacaine injection of 8 mg/kg is significantly higher than that of the vehicle group only at 0.5 h and 1 h after administration; the hot plate paw withdrawal time of SD rats with bupivacaine conjugate 10 injection of 32 mg/kg is significantly higher than that of the vehicle group at 0.5 h, 1 h, 2 h, 4 h, and 8 h after administration; the hot plate paw withdrawal time of SD rats with bupivacaine conjugate 11 injection of 24 mg/kg is significantly higher than that of the vehicle group within 6 h after administration; the hot plate paw withdrawal time of SD rats with bupivacaine conjugate 12 injection of 48 mg/kg is significantly higher than that of the vehicle group within 2 h after administration.

TABLE 12

Effect of PEG-bupivacaine conjugate on the hot plate paw withdrawal time of SD rats

| Groups | Drugs | Dose (mg/kg) | Before surgery | 0 h | 0.5 h | 1 h | 2 h | 4 h | 6 h | 8 h | 12 h | 24 h |
|---|---|---|---|---|---|---|---|---|---|---|---|---|
| G1 | Vehicle | — | 5.19 | 1.92 | 2.13 | 1.90 | 2.34 | 2.71 | 2.19 | 1.93 | 1.80 | 2.67 |
| G2 | bupivacaine | 8 | 5.40 | 2.28 | 7.39 | 9.22 | 2.81 | 1.89 | 1.78 | 1.95 | 2.43 | 1.72 |
| G3 | bupivacaine conjugate 10 | 32 | 4.98 | 2.41 | 6.52 | 10.12 | 11.43 | 9.83 | 8.10 | 6.91 | 1.96 | 2.18 |
| G4 | bupivacaine conjugate 11 | 24 | 5.15 | 2.14 | 7.43 | 8.49 | 9.10 | 8.31 | 7.10 | 1.97 | 2.71 | 2.76 |
| G5 | bupivacaine conjugate 12 | 48 | 5.51 | 1.89 | 8.13 | 7.21 | 6.12 | 2.98 | 2.91 | 2.18 | 1.85 | 2.56 |

Motor block (four-level score): The exercise condition of each group of rats is evaluated by the motor block four-level scoring method. The scoring criteria are: paws can be dorsiflexed, stretched, valgus and other normal exercises, scored by 1 point; paws can be dorsiflexed, bendable or after the adduction, although the paws can be stretched, the stretching ability is weakened, scored by 2 points; the paw can perform dorsiflexion, but no longer has the ability to stretch, scored by 3 points; the paw completely loses the ability of dorsiflexion, curling and stretching, and the rats produce a gait defect, scored by 4 points. The time point for determining the withdrawal time of the hot plate is before administration, and 0.5 h, 1 h, 2 h, 4 h, 6 h, 8 h, 12 h, and 24 h after administration.

The experimental results are shown in Table 13. From the data in Table 13, there is no significant difference in motor function scores of SD rats in each experimental group in the absence of administration. After direct injection for administration, from the results of sensory block and motor block, the bupivacaine conjugate 10 does not affect the motor function of SD rats when administered at 32 mg/kg, and the analgesic effect can reach 8 h; the bupivacaine conjugate 11 does not affect the motor function of SD rats when administered at 24 mg/kg, and the analgesic effect can reach 6 h or above; the bupivacaine conjugate 12 does not affect the motor function of SD rats when administered at 48 mg/kg, and the analgesic effect can reach 2 h.

The above embodiments are only the preferred embodiments of the present invention, and are not intended to limit the present invention. Any modifications, equivalent substitutions, etc., which are within the spirit and principles of the present invention, should be included in the protection scope of the present invention.

The invention claimed is:

1. A method of using a local anesthetic release system for non-anesthetic analgesia treatment, the method comprising: administering the local anesthetic release system to a subject, the local anesthetic release system is a prodrug of a local anesthetic, wherein the prodrug of the local anesthetic is a conjugate of polyethylene glycol and a local anesthetic, having a structure of a formula (I):

$$\text{PEG-A-R}_0\text{—B} \qquad (I)$$

wherein, PEG is a polyethylene glycol residue with a molecular weight of 1-100 KDa;
$R_0$ is a $C_{1-6}$ alkyl group;
B is a local anesthetic;
a quaternary ammonium salt having a structure of

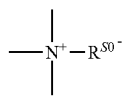

is formed at the junction of B and $R_0$, and $R^{s0}$ is selected from a group consisting of F⁻, Cl⁻, Br⁻, I⁻, mesylate, ethylsulfonate, benzenesulfonate, citrate, lactate, succinate, fumarate, glutamate, citrate, salicylate and maleate;
A is a linking group selected from a structure shown by the following formula $A_1$ or $A_2$:

TABLE 13

Effect of PEG-bupivacaine conjugate on motor function score of SD rats

| Groups | Drugs | Dose (mg/kg) | 0.5 h | 1 h | 2 h | 4 h | 6 h | 8 h | 12 h | 24 h |
|---|---|---|---|---|---|---|---|---|---|---|
| G1 | Vehicle | — | 1 ± 0 | 1 ± 0 | 1 ± 0 | 1 ± 0 | 1 ± 0 | 1 ± 0 | 1 ± 0 | 1 ± 0 |
| G2 | bupivacaine | 8 | 1 ± 0 | 1.75 ± 0.5 | 1.75 ± 0.5 | 1.75 ± 0.5 | 1.75 ± 0.5 | 1.75 ± 0.5 | 1 ± 0 | 1 ± 0 |
| G3 | bupivacaine conjugate 10 | 32 | 1 ± 0 | 1.75 ± 0.5 | 1.75 ± 0.5 | 1.75 ± 0.5 | 1.75 ± 0.5 | 1.75 ± 0.5 | 1 ± 0 | 1 ± 0 |
| G4 | bupivacaine conjugate 11 | 24 | 1 ± 0 | 1 ± 0 | 1 ± 0 | 1 ± 0 | 1 ± 0 | 1 ± 0 | 1 ± 0 | 1 ± 0 |
| G5 | bupivacaine conjugate 12 | 48 | 1 ± 0 | 1 ± 0 | 1 ± 0 | 1 ± 0 | 1 ± 0 | 1 ± 0 | 1 ± 0 | 1 ± 0 |

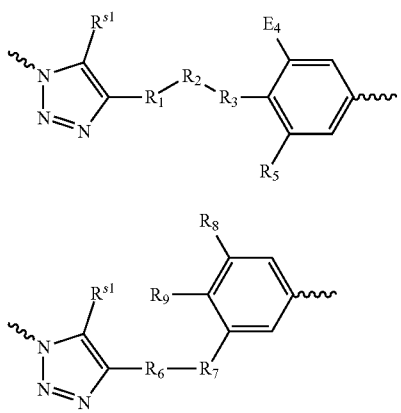

wherein, $R_1$ and $R_6$ are independently selected from a $C_{1-6}$ alkyl group, or $R_1$ and $R_6$ are independently selected from —$(CH_2)_i$NHCO$(CH_2)_j$—, or —$(CH_2)_i$CONH$(CH_2)_j$—, and i and j are independently an integer selected from 0 to 6;

$R_2$ is selected from —C=O, —C=S, —O— or —S—;

$R_3$ and $R_7$ are independently selected from —O— or —S—;

$R_4$ and $R_5$ are independently selected from H, $C_{1-6}$ alkyl or halogen;

$R_8$ and $R_9$ are independently selected from H, $C_{1-6}$ alkyl or —O(C=O)$(CH_2)_i$CH$_3$, and i is an integer selected from 0 to 6;

$R^{s1}$ is selected from H or $C_{1-6}$ alkyl.

2. The method according to claim 1, wherein the concentration of free local anesthetics released in the local tissue and/or systemic part is maintained between a minimum anesthetic dose and minimum analgesic dose of the local anesthetic after administration of the local anesthetic delivery system.

* * * * *